United States Patent [19]

Rinehart et al.

[11] Patent Number: 5,089,273
[45] Date of Patent: Feb. 18, 1992

[54] ECTEINASCIDINS 729, 743, 745, 759A, 759B AND 770

[75] Inventors: Kenneth L. Rinehart, Urbana, Ill.; Tom G. Holt, Westfield, N.J.

[73] Assignee: Board of Trustees of the University of Illinois, Urbana, Ill.

[21] Appl. No.: 548,060

[22] Filed: Jul. 5, 1990

Related U.S. Application Data

[63] Continuation-in-part of Ser. No. 278,629, Dec. 1, 1988, abandoned, which is a continuation of Ser. No. 1,226, Jun. 1, 1987, Continuation-in-part of Ser. No. 6,395, Jan. 23, 1987, abandoned, Continuation-in-part of Ser. No. 898,906, Aug. 21, 1986, abandoned, Continuation-in-part of Ser. No. 872,189, Jun. 9, 1986, abandoned.

[51] Int. Cl.[5] .............................................. A61K 35/56
[52] U.S. Cl. ..................................... 424/520; 530/855
[58] Field of Search ......................... 424/520; 530/855

[56] References Cited

PUBLICATIONS

Lichter et al., in Food and Drugs from the Sea Proceedings (1972), Marine Technology Society, Washington, D.C. 1973, pp. 117-127.

Primary Examiner—Douglas W. Robinson
Assistant Examiner—Jean C. Wite
Attorney, Agent, or Firm—Ernest V. Linek

[57] ABSTRACT

The present invention relates to novel compositions of matter extracted from the well-known and readily available tropical marine invertebrate, Ecteinascidia turbinata, and designated herein as ecteinascidins 729, 743, 745, 759A, 759B and 770. These compounds are useful as antibacterial and/or antitumor agents in mammals.

6 Claims, 2 Drawing Sheets

ECTEINASCIDINS 729, 743, 745, 759A, 759B AND 770

CROSS-REFERENCE TO RELATED APPLICATIONS

This application is a continuation-in-part of U.S. Ser. No. 07/278,629, filed 1 Dec. 1988, now abandoned, which is a continuation of PCT/US87/01226 filed 1 June 1987, which is a continuation-in-part of U.S.. Ser. No. 006,395, filed 23 Jan. 1987, now abandoned, which is a continuation-in-part of U.S. Ser. No. 898,906, filed 21 Aug. 1986, now abandoned, which is a continuation-in-part of U.S. Ser. No. 872,189, filed 9 June 1986, now abandoned.

FIELD OF THE INVENTION

The present invention relates to novel compositions of matter. More particularly, the present invention relates to novel antibacterial agents designated herein as ecteinascidins 729, 743, 745, 759A, 759B and 770. These compounds are extracted from the marine tunicate *Ecteinascidia turbinata*, which is a well-known and readily available tropical marine invertebrate. Biological activity has been assigned previously to extracts of *E. turbinata*; see, for example, M. M. Sigel et al., "Anticellular and Antitumor Activity of Extracts from Tropical Marine Invertebrates," in Food-Drugs from Sea Proceedings (1969), Youngken, H. W., Jr., Ed., Marine Technology Society, Washington, D.C., 1970, pp. 281-294; Lichter, W. et a., "Biological Activities Exerted by Extracts of *Ecteinascidia turbinata*," in Food-Drugs from the Sea Proceedings (1972), Worthen, L. R., Ed., Marine Technology Society: Washington D.C., 1973, pp. 117-127; Lichter, W., et al., "Inhibition of DNA Synthesis by *Ecteinascidia turbinata* Extracts (ETE)," in Food-Drugs from the Sea Proceedings, 1974, Webber, H. H., Ruggieri, G. D., Eds., Marine Technology Society: Washington, D.C., 1976, pp 395-401; and Lichter, W. et al., "Immunomodulation by Extracts of *Ecteinascidia turbinata*," in Drugs and Food From the Sea, Kaul, P. N., Sindermann, C. J., Eds., The University of Oklahoma, Norman, Okla., 1978, pp. 137-144.

INFORMATION DISCLOSURE STATEMENT

Extracts from *Ecteinascidia turbinata* are known, as described herein. Certain of these extracts are known to have biological activity.

SUMMARY OF THE INVENTION

The present invention particularly provides:

(1) Ecteinascidin 729, having the following physicochemical characteristics: TLC ($SiO_2$) $R_4$-0.28 (3:1 ethyl acetate-methanol), 0.26 (9:1 chloroform-methanol); HPLC retention time, 15.7 min. [Whatman Partisil 10 ODS-3, 10×250 mm, 70:30 methanol-aqueous Tris (0.05M, pH 7.5), 2.8 Ml/min.]; UV max ($CH_3OH$), 202 nm ($\epsilon$61 000), 244 (sh) (11 000), 283 (5 000), 289 (4 700), (0.1N HCL) 204 (61 000), 244 (sh) (9 600), 283 (4 800), 289 (4 500), (0.1N KOH) 215 (33 800), 258 (8 200), 290 (6 400); IR ($CCl_4$) 3555, 3535, 2953, 2927, 2855, 1770, 1742, 1504, 1466, 1462, 1454, 1432, 1369, 1239, 1196, 1168, 1122, 1100, 1086, 1054, 1032, 997, 960 cm$^{-1}$; $^1$H NMR (360 MHz, $CDCl_3$)$\delta$ 6.63 (s, 1H), 6.48 (s, 1H(, 6.44 (s, 1H), 6.04 (d, J-0.7 Hz, 1H), 5.95 (d, J-0.9 Hz, 1H), 5.15 (d, J-10.7 Hz, 1H), 4.84 (bs, 1H), 4.52 (d, J-3.5 Hz, 1H), 4.48 (bs, 1H), 4.38 (d, J-4.89 Hz, 1H), 4.04 (d, J-11 Hz, 1H), 3.78 (s, 3H), 3.62 (s, 3H), 3.61 (m, 2H), 3.10 (m, 1H), 3.02 (d, J-18 Hz, 1H), 2.90 (dd, J-9, 18 Hz, 1H), 2.80 (m, 1H), 2.60 (m, 1H), 2.50 (m, 1H), 2.35 (m, 1H), 2.31 (s, 3H), 2.27 (s, 3H), 2.20 (m, 1H), 2.03 (s, 3H); FABMS, m/z (rel. intensity) 730.2493 (30), 495 (2), 493 (2), 481 (2), 479 (2), 463 (4), 461 (2), 449 (4), 205 (8, 204 (8), 190 (8); B/E linked scan FABMS m/z 729→m/z 711, 696, 683, 509, 495, 481, 479, 461, 449; optical rotation $[\alpha]_D^{25}+112°$ (c 0.01, $CH_3OH$).

(2) Ecteinascidin 743, having the following physicochemical characteristics: TLC ($SiO_2$) $R_f$-0.58 (3:1 ethyl acetate-methanol), 0.44 (9:1 chloroform-methanol); HPLC retention time, 18.8 min. [Whatman Partisil 10 ODS-3, 10×250 mm, 70:30 methanol-aqueous Tris (0.05M, pH 7.5), 2.8 mL/min.]; UV max ($CH_3OH$) 202 nm ($\epsilon$81 000), 240 (sh) (15 000), 284 (6 600), 289 (6 400), (0.1N HCl) 205 (76 000), 240 (sh) (12 000), 285 (7 500), 289 (7 200), (0.1N KOH) 216 (50 000), 256 (12 700) 290 (9 000); IR ($CCl_4$) 3549, 3530, 2992 (weak), 2929, 2848, 2803 (weak), 1764, 1739, 1597 (weak), 1511, 1501, 1460, 1445, 1425, 1365, 1350, 1195, 1160, 1115, 1102, 1098, 1082, 1058, 1048, 1024, 990, 950, 915, 907 cm$^{-1}$, $^1$H NMR (500 Mhz, $CDCl_3$) $\delta$ 6.62 (s, 1H), 6.48 (s, 1H), 6.46 (s, 1H), 6.03 (d, J-1.2 Hz, 1H), 5.95 (d, J-1.3 Hz, 1H), 5.71 (bs, exchanges, 1H), 5.14 (dd, J-0.9, 11.3 Hz, 1H), 4.83 (bs, 1H), 4.50 (d, J-3.3 Hz, 1H), 4.50 (bs, 1H), 4.18 (d, J-4.2 Hz, 1H), 4.06 (dd, J-2.5, 11.3 Hz, 1H), 3.81 (s, 3H), 3.63 (s, 3H), 3.59 (bd, J-4.4 Hz, 1H), 3.23 (m, 1H), 3.14 (ddd, J-11, 10, 4 Hz, 1H), 2.91 (bd, J-18 Hz, 1H), 2.88 (dd, J-9, 18 Hz, 1H), 2.82 (m, 1H), 2.62 (ddd, J-16, 10, 4 Hz, 1H), 2.49 (ddd, J-16, 4, 4 Hz, 1H), 2.37 (bd, J-13.9 Hz, 1H), 2.33 (s, 3H), 2.28 (s, 3H), 2.19 (s, 3H), 2.18 (d, J-13.9 Hz, 1H), 2.04 (s, 3H); $^{13}$C NMR (75.4 MHz and 125.7 MHz, $CDCl_3$) $\delta$ 9.6 (q), 15.7 (q), 20.4 (q), 24.1 (t), 28.7 (t), 39.6 (t), 41.3 (q), 42.1 (t), 42.1 (d), 54.8 (d), 55.0 (q), 55.9 (d), 57.7 (d), 57.8 (d), 60.2 (q), 61.3 (t), 64.6 (s), 82.0 (d), 101.6 (t), 109.8 (d), 112.5 (s), 114.1 (d), 115.9 (s), 118.1 (s), 120.9 (d), 121.9 (s), 126.0 (s), 129.2 (s), 129.2 (s), 131.5 (s), 140.5 (s), 141.3 s), 143.0 (s), 144.3 (s), 144.5 (s), 145.1 (s), 147.5 (s), 168.3 (s), 172.5 (s); FABMS m/z (rel. intensity) 744.2648 (100), 699.2766 (4), 495.2064 (15), 477.1978 (15), 475 (9), 463.1837 (25), 218 (39), 204.1027 (71); LC/FABMS m/z (rel. intensity) 744 (34), 495 (12), 493 (16), 477 (14), 475 (10), 453 (14), 234 (42), 218 (64), 204 (100, 189 (62), 174 (28), 160 (22); EIMS m/z 217.0737305, 191.0941620, 176.0696716; ESCA (mole percent) C (73.1), O (20.4), N (5.2), S (1.3); optical rotation $[\alpha]_D^{25}+114°$ (c 0.1, $CH_3OH$); or a derivative thereof selected from the group consisting of: deacetyl-, dioxy-, diacetyl-, monoacetyl-, mono-O-methyl-, di-O-methyl-, monooxy-, tetracetyl-, or p-bromobenzoyl.

(3), Ecteinascidin 745, having the following physicochemical characteristic: TLC ($SiO_2$) $R_f$-0.42 (3:1 ethyl acetate-methanol, 0.38 (9:1 chloroform-methanol); HPLC retention time, 29.8 min. [Whatman Partisil 10 ODS-3, 10×250 mm, 70:30 methanol-aqueous Tris (0.05M, pH 7.5) 2.8 mL/min.]; UV max ($CH_3OH$) 202 ($\epsilon$ 52 000), 240 (sh) (11 000), 281 (5 600), 287 (5 400), (0.1N HCl), 204 (51 000), 240 (sh) (9 500), 281 (5 200), 287 (5 200), (0.1N KOH), 215 (36 000), 254 (8 500), 290 (5 900), 298 (5 800; IR ($CCl_4$) 3554, 3535, 2955, 2927, 2871, 2855, 1770, 1744, 1581, 1507, 1270, 1238, 1195, 1163, 1088, 1056 cm$^{-1}$; $^1$NMR (360 MHz, $CDCl_3$), 67 6.62 (s, 1H), 6.52 (s, 1H), 6.47 (s, 1H), 6.02 (d, J-1.2 Hz, 1H), 5.97 (d, J-1.2 Hz, 1H), 5.74 (bs, exchanges, 1H), 5.14 (d, J-11.2 Hz, 1H), 4.50 (bs, 1H), 4.22 (bs, 1H), 4.11 (dd, J-2, 11 Hz, 1H), 3.79 (s, 3H), 3.68 (s, 1H), 3.63 (s, 3H), 3.31 (m, 1H), 3.23 (bs, 1H), 3.11 (m, 2H), 2.93 (m, 2H), 2.69 (m, 2H), 2.54 (m, 2H), 2.44 (d, J-14 Hz, 1H), 2.33 (s, 3H), 2.28 (s, 3H), 2.18 (s, 3H), 2.13 (m, 1H), 2.04 (s, 3H); FABMS m/z (rel. intensity) 746.2775 (100), 699 (8), 631 (8), 629 (8) 495 (19), 479 (42), 477 (52), 463 (36), 205 (64), 204 (64); LC/FABMS /mz (rel. intensity) 746 (44), 495 (18), 477 (20), 463 (32), 218 (42), 204 (100), 189 (62), 176 (32), 160 (20); optical rotation $[\alpha]_D^{25} +50°$ (c 0.1, CH$_3$OH).

(4) Ecteinascidin 759A, having the following physicochemical characteristics: TLC (SiO$_2$) R$_f$-0.6 (3:1 ethyl acetate-methanol), 0.3 (9:1 chloroform-methanol); HPLC retention time, 11.0 min [Whatman Partisil 10 ODS-3, 10×250 mm, 70:30 methanol-aqueous Tris (0.05M, pH 7.5), 2.8 mL/min.]; UV max (CH$_3$OH) 203 nm ($\delta$ 43 000), 250 (sh) (6 500), 281 (3 000), 288 (2 600), (0.1N HCl) 205 (44 000), 250 (sh) (7 600), 281 (4 500), 288 (4 400), (0.1N KOH) 216 (39 000), 249 (9 300), 294 (4 600); IR (CCl$_4$) 3696, 3555, 3532, 2926, 2854, 1770, 1744, 1670, 1466, 1252, 1240, 1194, 1091 cm$^{-1}$; FABMS m/z (rel. intensity) 760.2563 (58), 581 (25), 493 (16), 463 (80), 461 (100); LC/FABMS m/z (rel. intensity) 760 (26), 509 (12), 493 (12), 463 (24), 449 (16), 246 (26), 232 (32), 224 (62), 218 (5), 204 (100), 189 (56), 174 (18), 160 (16), optical rotation $[\alpha]_D^{25} +130°$ (c 0.05, CH$_3$OH).

(5) Ecteinascidin 759B, having the following physicochemical characteristics: TLC (SiO$_2$) R$_f$-0.6 (3:1 ethyl acetate-methanol), 0.3 (9:1 chloroform-methanol); HPLC retention time, 13.9 min. [Whatman Partisil 10 ODS-3, 10×250 mm, 70:30 methanol-aqueous Tris (0.05M, pH 7.5), 2.8 mL/min.]; UV max (CH$_3$OH) 208 nm ($\epsilon$ 60 000(, 288 (4 800), 293 (4 500), (0.1N HCl) 209 (64 000), 288 (7 100), 293 (7 100), 0.1N KOH) 220 (45 000), 260 (10 000), 298 (7 600); IR (CCl$_4$), 3555, 2933, 1770, 1743, 1590, 1514, 1465, 1453, 1446, 1431, 1368, 1356, 1330, 1288, 1264, 1240, 1193, 1163, 1124, 1110, 1089, 1032, 1006, 821 cm$^{-1}$; FABMS m/z (rel. intensity) 760.2519 (100), 744 (71), 730 (19), 493 (29), 477 (43), 463 (76); LC/FABMS m/z (rel. intensity) 760 (38), 508 (8), 493 (18), 463 (26), 475 (14), 248 (30), 234 (48), 218 (86), 204 (100), 189 (56), 176 (26), 160 (32); optical rotation $[\alpha]_D^{25} +167°$ (c 0.1, CH$_3$OH).

(6) Ecteinascidin 770, having the following physicochemical characteristics: TLC (SiO$_2$) R$_f$-0.6 (3:1 ethyl acetate-methanol), 0.3 (9:1 chloroform-methanol); HPLC retention time, 12.0 min. [Whatman Partisil 10 ODS-3, 10×250 mm, 70:30 methanol-aqueous Tris (0.05M, pH 7.5), 2.8 mL/min.]; UV max (CH$_3$OH) 342 nm ($\delta$ 3 200), 329 (3 900), 299 (22 000), 263 (25 000), 240 (58 000), 234 (55 000), 216 (66 000), 0.1N HCl) 342 (4 900), 329 (5 700), 299 (24 000), 263 (29 000), 240 (58 000), 234 (57 000), 216 (71 000), (0.1N KOH) 342 (3 700), 329 (4 900), 299 (22 000), 263 (28 000), 240 (58 000), 234 (57 000), 227 (57 000); IR (CCl$_4$) 3555, 3535, 3484, 2929, 2910, 1770, 1742, 1607, 1516, 1509, 1504, 1494, 1462, 1450, 1433, 1325, 1237, 1193, cm$^{-1}$; $^1$H NMR (300 MHz, CDCl$_3$), $\delta$ 6.60 (s, 1H), 6.47 (s, 1H), 6.45 (s, 1H, 6.05 (s, 1H), 5.98 (s, 1H), 5.02 (d, j-11.4 Hz, 1H), 4.57 (bs, 1H), 4.32 (bs, 1H), 4.28 (d, j-5.3 Hz, 1H), 4.18 (d, J-2.5 Hz, 1H), 4.12 (dd, J-2.1, 11.5 Hz, 1H), 3.78 (s, 3H), 3.62 (s, 3H), 3.50 d, J-5 Hz, 1H), 3.42 (m, 1H), 3.10 (ddd, J-4, 10, 11 Hz, 1H), 2.94 (m, 2H), 2.79 (m, 1H), 2.61 (m, 1H), 2.47 (m, 1H), 2.34 (m, 1H), 2.32 (s, 3H), 2.27 (s, 3H), 2.20 (s, 3H), 2.09 (m, 3H), 2.04 (s, 3H)FABMS m/z (rel. intensity) 771.2700 (48), 760 (8), 744 (20), 723 (12), 488 (12), 463 (14), 461 (20), 205 (50), 204 (80); optical rotation $[\not=]_D^{25} +52°$ (c 0.1, CH$_3$OH).

The organism from which the ecteinascidins were extracted is a marine colonial tunicate identified as *Ecteinascidia turbinata* by Dr. Francoise Lafargue, Université de Paris VI, Laboratoire Arago, Banyuls-sur-Mer, France. *E. turbinata* belongs to the family Perophoridae, suborder Phlebobrachia, order Enterogona, class Ascidiacea, subphylum Tunicata, phylum Chordata. Detailed descriptions of this readily available organism can be found in the following references, the disclosures of which, to the extent necessary, are hereby incorporated herein by reference:

1. W. G. VanName, "The Ascidians of the Bermuda Islands", *Trans. Conn. Acad. Arts Sci.*, 11, 325–412 (1902). See pages 338–339 for a description of *E. turbinata*.

2. W. G. Van Name, "The North and South American Ascidians", *Bull. Amer. Museum Nat. Hist.*, 84, 1–476 (1945). See plate 20, text figures 82A, 85, 86, and pages 169–171 for a complete description of *E. turbinata* and a comprehensive list of previous references.

3. H. H. Plough, "Sea Squirts of the Atlantic Continental Shelf from Maine to Texas", John Hopkins University Press, 1978, Baltimore, Md. See text figures 13, 30e, and pages 22–22, 54, and 68 for descriptions of *E. turbinata*.

*E. turbinata* is common and widely distributed in the Caribbean. It is conspicuous on account of the large size and often bright orange color of the colonies. A colony consists of a dense cluster of elongated, club-shaped zooids, which are connected at their tapered bases by a network of stolons that adheres to the surface of the object on which the colony grows. Colonies are found in shallow water (0–20 feet) growing on mangrove roots, sponges, rocks, shells, turtle grass, bridge pilings, bottom sand, stone, or the like. The animals are easily collected by wading, snorkeling, or SCUBA techniques.

Samples have been obtained in the following locations:

1. On islands and shores of the Indian River near the Smithsonian Tropical Research Center, Harbor Branch Foundation, Fort Pierce, Fla., 27° 27'N by 80° 20' W.

2. Between No Name Key and Big Pine Key (especially on wooden pilings), Fla., 24° 42' N by 81° 21' W.

3. In the Sunshine Key Resort boat harbor of Ohio Key, Fla., 24° 40' N by 81° 14' W.

4. In the Keys near St. George's Cay and Drowned Cay, Belize, 17.5 N by 88° W.

The compounds of this invention, extracted from *E. turbinata*, exhibit antibacterial properties and thus are useful alone or in combination with other antibacterial agents to prevent the growth of or reduce the number of susceptible bacteria in many environments.

Certain compounds of the present invention have been shown to inhibit L1210 cells and P388 leukemia cells. Thus, the compounds of this invention are useful as antitumor agents. Therefore, they are useful to inhibit the growth of tumor cells in mammals exhibiting such tumor cells. Illustratively, dosage levels of the administered active ingredients can be intravenous, 0.1 to about 200 mg/kg; intraperitoneal, 1 to about 500 mg/kg/ subcutaneous, 1 to about 500 mg/kg; intramuscular, 1 to about 500 mg/kg; oral, 5 to about 1000 mg/kg; intranasal instillation, 5 to about 1000 mg/kg; and aerosol, 5 to about 1000 mg/kg of animal (body) weight.

The compounds of the present invention are preferably presented for administration to humans and animals in unit dosage forms, such as tablets, capsules, pills, powder, granules, suppositories, syrup, sterile parenteral solutions with suspensions, sterile non-parenteral solutions with suspensions, and oral solutions or suspensions and the like, containing high active quantities of the active ingredient. Those of ordinary skill in the art of pharmaceutical compositions can readily formulate compounds of the present invention into appropriate pharmaceutical compositions.

The administration of the compounds claimed herein is useful to inhibit the growth of cancer cells in animals or humans bearing a neoplastic disease, for example, acute myelocystic leukemia, acute lymphocystic leukemia, malignant melanoma, adenocarcinoma of the lung, neuroblastoma, small cell carcinoma of the lung, breast carcinoma, colon carcinoma, bladder carcinoma, and the like.

DETAILED DESCRIPTION OF THE PREFERRED EMBODIMENT

As described above, the present invention relates to novel compositions of matter extracted from the well-known and readily available tropical marine invertebrate, *Ecteinascidia turbinata*, and designated herein as ecteinascidins 729, 743, 745, 759A, 759B and 770. These compounds are useful as antibacterial and/or antitumor agents in mammals. The present invention will best be understood by reference to the following examples, which are not to be construed as limiting the present invention in any manner.

EXAMPLE 1

Isolation and Purification

The isolation and purification procedure was monitored at each step by performing thin-layer chromatography (TLC), in vitro antimicrobial assays, in vitro cytotoxicity assays, and bioautography on in vitro microbial organisms and tissue cell lines.

Countercurrent chromatography (CCC) employed the Ito Multi-Layer Coil Separator-Extractor (P. C. Inc.) with a #10 coil, a Milton Roy pump, and a LKB Uvicord II Ultraviolet (UV) detector (254, 280 nm; 3 mm flow cell). Medium pressure liquid chromatography (MPLC) was carried out with a Milton Roy pump, Ace Glass Michel-Miller Chromatography Columns, and a LKB Uvicord detector (280 nm, 3 mm flow cell). Analytical TLC and bioautography were carried out on E. Merck silica gel 60 F-254 analytical TLC plates. The plates were developed in 3:1 ethyl acetate-methanol or 9:1 chloroform-methanol solvent systems and visualized with iodine vapor or a 5% solution of phosphomolybdic acid in ethanol. UV spectra were obtained in methanol on a Perkin-Elmer Lambda 3 spectrophotometer. Infrared (IR) spectra were obtained in carbon tetrachloride or chloroform on a Nicolet 7000 Fourier Transform (FT)-IR. High performance liquid chromatography (HPLC) was carried out on a Whatman Partisil 10 ODS-3 column (10×250 mm) and employed a Beckman 110A solvent pump and a Beckman 153 UV detector (254 nm).

Nuclear magnetic resonance (NMR) spectra were obtained on Bruker 500, General Electric 300, and Nicolet NT-360 spectrometers. Chemical shifts for $^1$H and $^{13}$C NMR spectra are reported in ppm from tetramethylsilane. Low- and high-resolution fast atom bombardment (FAB) mass spectra were obtained on VG ZAB and VG Micromass 7070 spectrometers. Low- and high-resolution electron ionization (EI) mass spectra were carried out on a VG ZAB mass spectrometer. Liquid chromatography/FAB mass spectrometry (LC/FABMS) employed an Alltech $C_{18}$ microbore HPLC column (10 μm, 1×250 nm) with a Beckman 114 solvent pump, a modified VG moving belt interface for operation in the FAB mode, and a VG ZAB mass spectrometer. Metastable ion measurements employed the B/E linked scan technique on a VG ZAB SE spectrometer.

Figure 1:
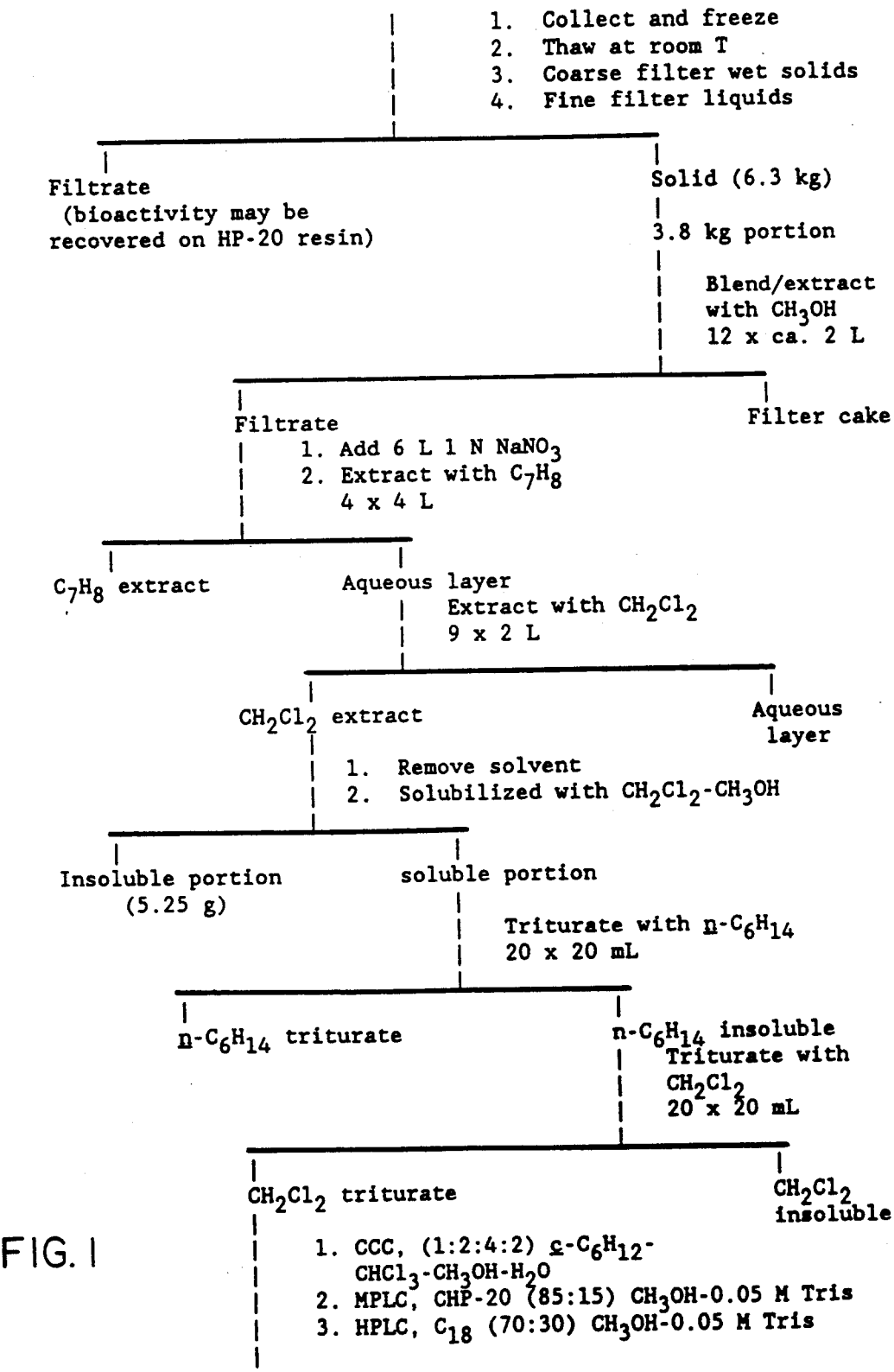
FIG. 1 illustrates an isolation scheme for the isolation of the ecteinascidins 729, 743, 745, 759A and 759B of the present invention from *Ecteinascidia turbinata* as described herein.

*Ecteinascidia turbinata* was collected in the Florida Keys at a depth of 0.2 to 15 feet. The sample was frozen until it was extracted by the following procedure. (Refer to FIG. 1.)

A sample of frozen tunicate (30.5 kg, wet weight) was thawed at room temperature and separated by coarse filtration into liquid and solid (6.3 kg) portions. A sample of the solid portion (3.8 kg) was extracted 12 time with methanol in a blender. The residue was filtered after each extraction to give a total of 20 L of methanol extract. The methanol extract was partitioned into an upper "organic" layer and a lower "polar" layer by adding 1N aqueous $NaNO_3$ (6 L) and toluene (4 L). The aqueous phase was extracted an additional 3 time with toluene (4 L), and the toluene extracts were combined and evaporated under reduced pressure to give 26.9 g of a dark green oil. The resulting aqueous phase was extracted with dichloromethane (9×2 L), and these extracts were combined and evaporated under reduced pressure to yield 15.9 g of a dark green solid.

The dichloromethane extract was solubilized successively with dichloromethane and methanol, leaving a 5.3 g insoluble beige portion. The soluble portion was evaporated under reduced pressure to give 10.6 g of a dark green solid. This material was triturated successively with hexane (20×20 mL) and dichloromethane (20×20 mL). The dichloromethane triturate (1.02 g) was purified by CC (2×0.51 g) using a cyclohexane-chloroform-methanol-water solvent system (1:2:4:2) to give 8 fractions. Fractions were evaluated by TLC bioautography.

An early bioactive CCC fraction (300 mg) was chromatographed on a CHP-20 porous polymer MPLC column (18×350 mm) using a methanol-aqueous tris(-hydroxymethyl)aminomethane (Tris) (0.05M, pH 7.5) step gradient (85:15, 90:10, 95:5, 100:0). The chromatography was followed by UV detection (280 nm). Fractions were collected and Tris was removed using a $C_{18}$ Sep-Pak, eluting first with water (to remove Tris), then with methanol (to recover sample). The major bioactive component was purified further by HPLC (Whatman Partisil 10 ODS-3, 10×250 mm) using a 70:30 methanol-aqueous Tris (0.05M, pH 7.5) solvent system to yield, after Tris removal, ecteinascidin 743 (27 mg) and ecteinascidin 745 (4.3 mg).

A later bioactive CCC fraction (69 mg) was chromatographed on a CHP-20 porous polymer MPLC column (18×350 mm) using a methanol-aqueous Tris (0.05M, pH 7.5) step gradient (80:20, 85:15, 90:10, 100:0). The chromatography was followed by UV detection (280 nm). Tris was removed from the fractions as above. The major bioactive component was purified further by HPLC (Whatman Partisil 10 ODS-3, 10×250 mm). using a 70:30 methanol-aqueous Tris (0.05M, pH 7.5) solvent system to yield, after Tris removal, ecteinascidin 729 (2.5 mg).

EXAMPLE 2

*E. turbinata* was extracted in a procedure similar to Example 1. A sample of the dichloromethane triturate (2.94 g) of the dichloromethane extract was purified by CCC (6×0.49 g) using a cyclohexane-chloroform-methanol-water solvent system (1:2:4:2) to give 10 fractions. Fractions were evaluated by TLC bioautography.

An early bioactive CCC fraction (200 mg) was further purified by CCC using a hexane-ethyl acetate-methanol-water (1:1:1:1) solvent system. A bioactive fraction (30 mg) was chromatographed on a CHP-20 porous polymer MPLC column (18×350 mm) using a methanol-water solvent system (85:15) buffered to pH 8.8 with 0.1% triethylamine acetic acid. The chromatography was followed by UV detection (280 nm). The major bioactive peak was collected (15.3 mg) and analyzed by LC/FABMS. LC/FABMS indicated one major component, ecteinascidin 743, and 3 minor components, ecteinascidin 745, ecteinascidin 759A, and ecteinascidin 759B.

PHYSICAL CHARACTERIZATION OF THE ECTEINASCIDINS (1) Ecteinascidin 729 has the following physicochemical characteristics: TLC (SiO$_2$) R$_f$ 0.28 (3:1 ethyl acetate-methanol), 0.26 (9:1 chloroform-methanol); HPLC retention time, 15.7 min. [Whatman Partisil 10 ODS-3, 10×250 mm, 70:30 methanol-aqueous Tris (0.05M, pH 7.5), 2.8 mL/min.]; UV max (CH$_3$OH), 202 nm ($\epsilon$ 61 000), 244 (sh) (11 000), 283 (5 000), 289 (4 700), (0.1N HCl) 204 (61 000), 244 (sh) (9 600), 283 (4 800), 289 (4 500), (0.1N KOH) 215 (33 800), 258 (8 200), 290 (6 400); IR (CCl$_4$) 3555, 3535, 2953, 2927, 2855, 1770, 1742, 1504, 1466, 1462, 1454, 1432, 1369, 1239, 1196, 1168, 1122, 1100, 1086, 1054, 1032, 997, 960 cm$^{-1}$; $^1$H NMR (360 MHz, CDCl$_3$) $\delta$ 6.63 (s, 1H), 6.48 (s, 1H), 6.44 (s, 1H), 6.04 (d, J-0.7 Hz, 1H), 5.95 (d, J-0.9 Hz, 1H), 5.15 (d, J-10.7 Hz, 1H), 4.84 (bs, 1H), 4.52 (d, J-3.5 Hz, 1H), 4.48 (bs, 1H), 4.38 (d, J-4.9 Hz, 1H), 4.04 (d, J-11 Hz, 1H), 3.78 (s, 3H), 3.62 (s, 3H), 3.61 (m, 2H), 3.10 (m, 1H), 3.02 (d, J-18 Hz, 1H), 2.90 (dd, J-9, 18 Hz, 1H), 2.80 (m, 1H), 2.60 (m, 1H), 2.50 (m, 1H), 2.35 (m, 1H), 2.31 (s, 3H), 2.27 (s, 3H), 2.20 (m, 1H), 2.03 (s, 3H); FABMS, m/z (re. intensity) 730.2493 (30), 495 (2), 493 (2), 481 (8), 479 (2), 463 (4), 461 (2), 449 (4), 205 (8), 204 (8), 190 (8); B/E linked scan on m/z 729, m/z 711, 696, 683, 509, 495, 481, 479, 461, 449; optical rotation $[\alpha]_D^{25}$ +112° (c 0.01, CH$_3$OH).

(2) Ecteinascidin 743 has the following physicochemical characteristics: TLC (SiO$_2$) R$_f$ 0.58 (3:1 ethyl acetate-methanol), 0.44 (9:1 chloroform-methanol); HPLC retention time, 18.8 min. [Whatman Partisil 10 ODS-3, 10×250 mm, 70:30 methanol-aqueous Tris (0.05M, pH 7.5), 2.8 mL/min.]; UV max (CH$_3$OH) 202 nm ($\epsilon$ 81 000), 240 (sh) (15 000), 284 (6 600), 289 (6 400), (0.1N HCl) 205 (76 000), 240 (sh) (12 000), 285 (7 500), 289 (7 200), (0.1N KOH) 216 (50 000), 256 (12 700) 290 (9 000); IR (CCl$_4$) 3549, 3530, 2992 (weak), 2929, 2848, 2803 (weak), 1764, 1739, 1597 (weak), 1511, 1501, 1460, 1445, 1425, 1365, 1350, 1195, 1160, 1115, 1102, 1098, 1082, 1058, 1048, 1024, 990, 950, 915, 907 cm$^{-1}$; $^1$H NMR (500 MHz, CDCl$_3$) $\delta$ 6.62 (s, 1H), 6.48 (s, 1H), 6.46 (s, 1H), 6.03 (d, J-1.2 Hz, 1H), 5.95 (d, J-1.3 Hz, 1H), 5.71 (bs, exchanges, 1H), 5.14 (dd, J-0.9, 11.3 Hz, 1H), 4.83 (bs, 1H), 4.50 (d, J-3.3 Hz, 1H), 4.50 (bs, 1H), 4.18 (d, J-4.2 Hz, 1H), 4.06 (dd, J-2.5, 11.3 Hz, 1H), 3.81 (s, 3H), 3.63 (s, 3H), 3.59 (bd, J-4.4 Hz, 1H), 3.23 (m, 1H), 3.14 (ddd, J-11, 10, 4 Hz, 1H), 2.91 (bd, J-18 Hz, 1H), 2.88 (dd, J-9, 18 Hz, 1H), 2.82 (m, 1H), 2.62 (ddd, J-16, 10, 4 Hz, 1H), 2.49 (ddd, J-16, 4, 4 Hz, 1H), 2.37 bd, J-13.9 Hz, 1H), 2.33 (s, 3H), 2.28 (s, 3H), 2.19 (s, 3H), 2.18 (d, J-13.9 Hz, 1H), 2.04 (s, 3H): $^{13}$C NMR (75.4 MHz and 125.7 MHz, CDCl$_3$) $\delta$ 9.6 (q), 15.7 (q), 20.4 (q), 24.1 (t), 28.7 (t), 39.6 (t), 41.3 (q), 42.1 (t), 42.1 (d), 54.8 (d), 55.0 (q), 55.9 (d), 57.7 (d), 57.8 (d), 60.2 (q), 61.3 (t), 64.6 (s), 82.0 (d), 101.6 (t), 109.8 (d), 112.5 (s), 114.1 (d), 115.9 (s), 118.1 (s), 120.9 (d), 121.9 (s), 126.0 (s), 129.2 (s), 129.2 (s), 131.5 (s), 140.5 (s), 141.3 (s), 143.0 (s), 144.3 (s), 144.5 (s), 145.1 (s), 147.5 (s), 168.3 (s), 172.5 (s); FABMS m/z (rel. intensity) 744.2648 (100), 699.2766 (4), 495.2064 (15), 477.1978 (15), 475 (9), 463.1837 (25), 218 (39), 204.1027 (71); LC/FABMS m/z (rel. intensity) 744 (34), 495 (12), 493 (16), 477 (14), 475 (10), 463 (14), 234 (42), 218 (64), 204 (100), 189 (62), 174 (28), 160 (22); EIMS m/z 217.0737305, 191.0941620, 176.0696716; ESCA (mole percent) C (73.1), O (20.4), N (5.2), S (1.3); optical rotation $[\alpha]_D^{25}$ +114° (c 0.1, CH$_3$OH).

(3) Ecteinascidin 745 has the following physicochemical characteristics: TLC (SiO$_2$) R$_f$ 0.42 (3:1 ethyl acetate-methanol, 0.38 (9:1 chloroform-methanol); HPLC retention time, 29.8 min. [Whatman Partisil 10 ODS-3, 10×250 mm, 70:30 methanol-aqueous Tris (0.05M, pH 7.5), 2.8 mL/min.]; UV max (CH$_3$OH) 202 ($\epsilon$ 52 000), 240 (sh) (11 000), 281 (5 600), 287 (5 400), (0.1N HCl), 204 (51 000), 240 (sh) 9 500), 281 (5 200), 287 (5 200), (0.1N KOH), 215 (36 000), 254 (8 500), 290 (5 900), 298 (5 800); IR (CCl$_4$) 3554, 3535, 2955, 2927, 2871, 2855, 1770, 1744, 1518, 1507, 1270, 1238, 1195, 1163, 1088, 1056 cm$^{-1}$; $^1$H NMR (360 MHz, CDCl$_3$), $\delta$ 6.62 (s, 1H), 6.52 (s, 1H), 6.47 (s, 1H), 6.02 (d, J-1.2 Hz, 1H), 5.97 (d, J-1.2 Hz, 1H), 5.74 (bs, exchanges, 1H), 5.14 (d, J-11.2 Hz, 1H), 4.50 (bs, 1H), 4.22 (bs, 1H), 4.11 (dd, J-2, 11 Hz, 1H), 3.79 (s, 3H), 3.68 (s, 1H), 3.63 (s, 3H), 3.31 (m, 1H), 3.23 (bs, 1H), 3.11 (m, 2H), 2.93 (m, 2H), 2.69 (m, 2H), 2.54 (m, 2H), 2.44 d, J-14 Hz, 1H), 2.33 (s, 3H), 2.28 (s, 3H), 2.18 (s, 3H), 2.13 (m, 1H), 2.04 (s, 3H); FABMS m/z (rel. intensity) 746.2775 (100), 699 (8), 631 (8), 629 (8), 495 (19), 479 (42), 477 (52), 463 (36), 205 (64), 204 (64); LC/FABMS m/z (rel. intensity) 746 (44), 495 (18), 477 (20), 463 (32), 218 (42), 204 (100), 189 (62), 176 (32), 160 (20); optical rotation $[\alpha]_D^{25}$ +50° (c, 0.1, CH$_3$OH).

(4) Ecteinascidin 759A has the following physicochemical characteristics: TLC (SiO$_2$) R$_f$ 0.6 (3:1 ethyl acetate-methanol), 0.3 (9:1 chloroform-methanol); HPLC retention time, 11.0 min. [Whatman Partisil 10 ODS-3, 10×250 mm, 70:30 methanol-aqueous Tris (0.05M, pH 7.5), 2.8 mL/min.]; UV max (CH$_3$OH) 203 nm ($\delta$ 43 000), 250 (sh) (6 500), 281 (3 000), 288 (2 600), (0.1N HCl) 205 (44 000), 250 (sh) (7 600), 281 (4 500), 288 (4 400), 0.1N KOH) 216 (39 000), 249 (9 300), 294 (4 600); IR (CCl$_4$) 3696, 3555, 3532, 2926, 2854, 1770, 1744, 1670, 1466, 1252, 1240, 1194, 1091 cm$^{-1}$; FABMS m/z (rel. intensity) 760.2563 (58), 581 (25), 493 (16), 563 (80), 461 (100); LC/FABMS m/z (rel. intensity) 760 (26), 509 (12), 493 (12), 463 (24), 449 (16), 246 (26), 232 (32), 224 (62), 218 (5), 204 (100), 189 (56), 174 (18), 160 (16); optical rotation $[\alpha]_D^{25}$ +130° (c 0.05, CH$_3$OH). (5) Ecteinascidin 759B has the following physicochemical characteristics: TLC (SiO$_2$) R$_f$ 0.6 (3:1 ethyl acetate-methanol), 0.3 (9:1 chloroform-methanol); HPLC retention time, 13.9 min. [Whatman Partisil 10 ODS-3, 10×250 mm, 70:30 methanol-aqueous Tris (0.05M, pH 7.5), 2.8 mL/min.]; UV max (CH$_3$OH) 208 nm ($\epsilon$ 67 600), 288 (4 800), 293 (4 500), 0.1N HCl) 209 (64 000), 288 (7 100), 293 (7 100), 0.1N KOH) 220 (45 000), 260 (10 000), 298 (7 600); IR (CCl$_4$), 3555, 2933, 1770, 1743, 1590, 1514, 1465, 1453, 1446, 1431, 1368, 1356, 1330, 1288, 1264, 1240, 1193, 1163, 1124, 1110, 1089, 1032, 1006, 821 cm$^{-1}$; FABMS m/z (rel. intensity) 760.2519 (100), 744 (71), 730 (19), 493 (29), 477 (43), 463 (76); LC/FABMS m/z (rel. intensity) 760 (38), 508 (8), 493 (26), 475 (14), 248 (30), 234 (48), 218 (86), 204 (100), 189 (56), 176 (26), 160 (32); optical rotation [$\alpha$]$_D^{25}$+167° (c 0.1, CH$_3$OH).

EXAMPLE 3

Isolation of Ecteinascidin 770

Figure 2:
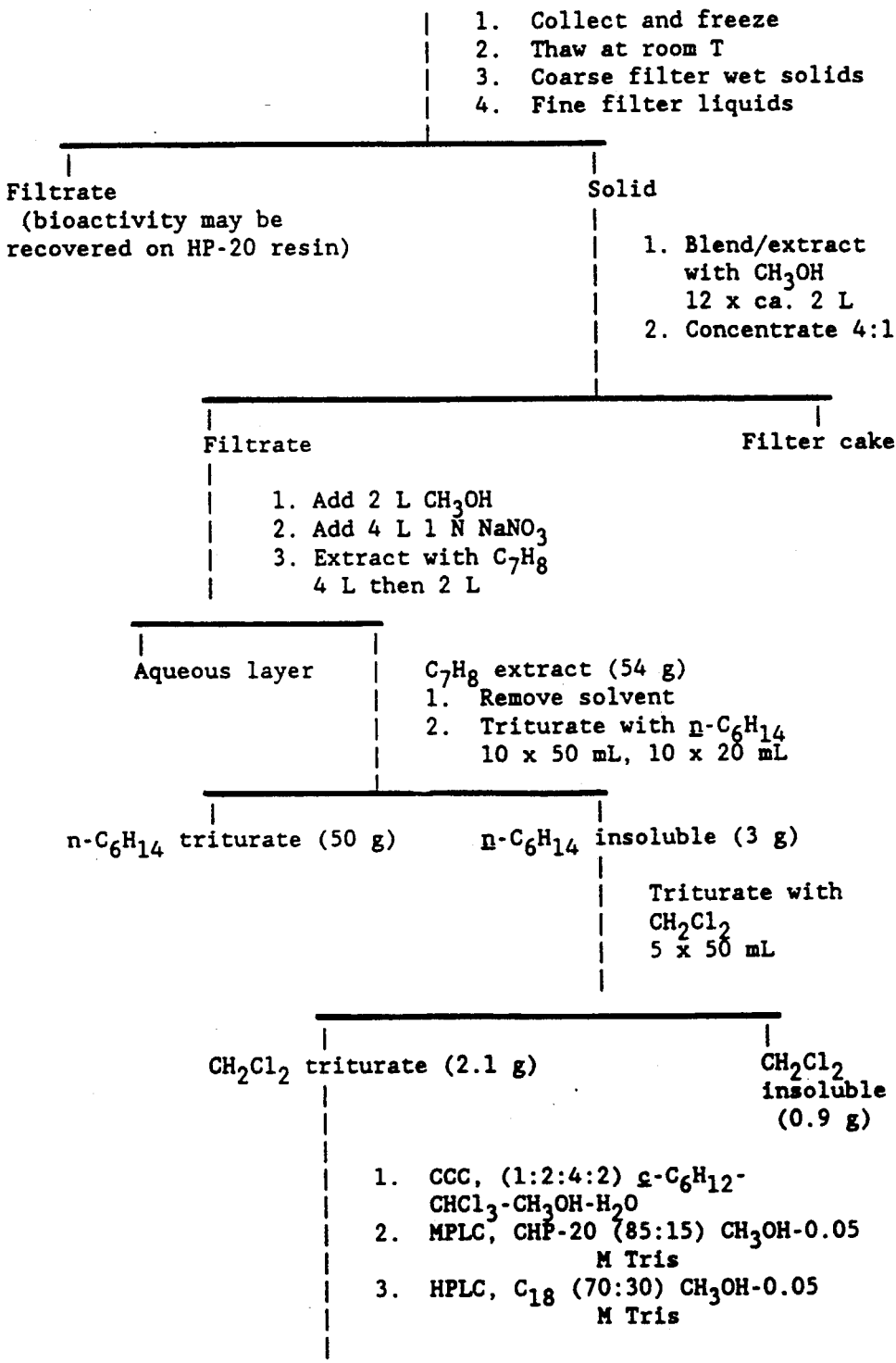
FIG. 2 illustrates an isolation scheme for the isolation of the Ecteinascidins 743, 759A, 759B and 770 of the present invention from *Ecteinascidia turbinata* as described herein.

*E. turbinata* (48 kg) is extracted in a procedure similar to Example 1, and illustrated schematically in FIG. 2. The methanol extract was partitioned into an upper "organic" layer and a lower "polar" layer by adding 1N aqueous NaNO$_3$ (4 L) and toluene (4 L, then 2 L). The toluene extracts were combined and evaporated under reduced pressure to produce a dark green oil (54 g). This material was triturated successively with hexane (10×50 mL, 10×20 mL), and dichloromethane (5×50 mL), to give a hexane triturate (50 g) and a dichloromethane triturate (2.1 g). A portion of the dichloromethane triturate (1.2 g) was purified by CCC (3×400 mg) using a cyclohexane-chloroform-methanol-water (1:2:4:2) solvent system to give 4 fractions.

An early bioactive CCC fraction (500 mg) was chromatographed on a CHP-20 porous polymer MPLC column (18×350 mm) using a methanol-0.05M Tris (85:15) solvent system and UV detection (280 nm). Two bioactive peaks were collected. The first bioactive peak was purified by HPLC (70:30 methanol-0.05M Tris, pH 7.5) to yield, after removal of buffer, ecteinascidin 759A (7 mg), ecteinascidin 759B (6 mg), and ecteinascidin 743 (5 mg). The second bioactive peak was purified by HPLC (70:30 methanol-0.5M Tris, pH 7.5) to yield, after removal of buffer, ecteinascidin 770 (12 mg).

Ecteinascidin 770 has the following physicochemical characteristics: TLC (SiO$_2$) R$_f$ 0.6 (3:1 ethyl acetate-methanol), 0.3 (9:1 chloroform-methanol); HPLC retention time, 12.0 min. [Whatman Partisil 10 ODS-3, 10×250 mm, 70:30 methanol-aqueous Tris (0.05M, pH 7.5), 2.8 mL/min.]; UV max (CH$_3$OH) 342 nm ($\epsilon$ 3 200), 329 (3 900), 299 (22 000), 263 (25 000), 240 (58 000), 234 (55 000), 216 (66 000), (0.1N HCl) 342 (4 900), 329 (5 700), 299 (24 000), 263 (29 000), 240 (58 000), 234 (57 000), 216 (71 000), (0.1N KOH) 342 (3 700), 329 (4 900), 299 (22 000), 263 (28 000), 240 (58 000), 234 (57 000), 227 (57 000); IR (CCl$_4$) 3555, 3535, 3484, 2929, 2910, 1770, 1742, 1607, 1516, 1509, 1504, 1494, 1462, 1450, 1433, 1325, 1237, 1193 cm$^{-1}$; $^1$H NMR (300 MHz, CDCl$_3$), $\delta$ 6.60 (s, 1H), 6.47 (s, 1H), 6.45 (s, 1H), 4.32 (bs, 1H), 4.28 (d, J-5.3 Hz, 1H), 4.18 (d, J-2.5 Hz, 1H), 4.12 (dd, J-2.1, 11.5 Hz, 1H), 3.78 (s, 3H), 3.62 (s, 3H), 3.50 (d, J-5 Hz, 1H), 3.42 (m, 1H), 3.10 (ddd, J-4, 10, 11 Hz, 1H), 2.94 (m, 2H), 2.79 (m, 1H), 2.61 (m, 1H), 2.47 (m, 1H), 2.34 (m, 1H), 2.32 (s, 3H), 2.27 (s, 3H), 2.20 (s, 3H), 2.09 (m, 1H), 2.04 (s, 3H); FABMS m/z (re. intensity) 771 (48), 760 (8), 744 (20), 723 (12), 488 (12), 463 (14), 461 (20), 205 (50), 204 (80); optical rotation [$\alpha$]$_D^{25}$+52° (c 0.1, CH$_3$OH).

Anal. Calcd for C$_{40}$H$_{43}$N$_4$O$_{10}$S: 771.2700 (M+H). Found: 771.2682 (HRFABMS).

EXAMPLE 4

Antibacterial Activity

| Compound | Mass/disk ($\mu$g) | Zone of inhibition (mm) |
|---|---|---|
| Ecteinascidin 743 | 0.2 | 17 |
| | 0.1 | 14 |
| | 0.05 | 12 |
| | 0.02 | 9 |
| | 0.01 | 7 |
| | 0.005 | trace |
| Ecteinascidin 745 | 40 | 7 |
| | 20 | trace |
| Ecteinascidin 729 | 0.250 | 22 |
| | 0.125 | 20 |
| | 0.063 | 19 |
| Ecteinascidin 759A | 1 | 9 |
| | 0.1 | — |
| Ecteinascidin 759B | 1 | 15 |
| | 0.1 | 9 |
| Ecteinascidin 770 | 1 | 14 |
| | 0.1 | trace |

EXAMPLE 5

L1210 Tube Dilution Assay

The compounds of this invention were shown to inhibit the growth of L1210 mouse leukemia cells in vitro as shown in the following table. The L1210 tube dilution assay is described in detail in a publication by L. H. Li, et al., *Cancer Research*, 39:4816 (1979). ID$_{50}$ and ID$_{90}$ refer to the concentration of ecteinascidin needed to inhibit cell growth by 50 to 90 percent, respectively.

| Compound | ID$_{50}$ ($\mu$g/mL) | ID$_{90}$ ($\mu$g/mL) |
|---|---|---|
| Ecteinascidin 743 | 0.0005 | 0.0017 |
| Ecteinascidin 745 | 0.088 | 0.19 |

EXAMPLE 6

In Vivo Testing of Ecteinascidins Against P388 Leukemia

Compounds of this invention are also active in vivo against P388 leukemia in mice. The P388 mouse leukemia test is described in detail in a publication by G. L. Neil et al., *Cancer Treatment Reports*, 63: 1971–1978 (1979). The results of three P388 mouse leukemia tests using different dosage schedules are shown below.

| Compound | Dose (mg/kg) | T/C |
|---|---|---|
| Ecteinascidin 743 | 0.063 | toxic |
| | 0.031 | 161 |
| Ecteinascidin 745 | 0.25 | ca. 100 |

EXAMPLE 7

Chemical Degradation of Ecteinascidin 743

Part A. Treatment with KOH

Ecteinascidin 743 (1.0 mg, 1.3 $\mu$mol) is dissolved in methanolic KOH (0.2N), and stirred at room temperature. The reaction is followed by HPLC [Whatman Partisil 5 ODS-3, 4.6×250 mm, 70:30:MeOH:0.05M Tris (pH 7.5), 1.5 mL/min.]. The product peak is observed immediately (3 min.) by HPLC. After the reaction is complete (45 min.), the reaction mixture is neutralized with methanolic HCl (0.5M) and the solvent is removed under a stream of nitrogen. The product is taken up in methanol, filtered, and purified with HPLC to yield deacetylecteinascidin 743 (0.8 mg, 85%).

Deacetylecteinascidin 743 has the following physicochemical characteristics: pale yellow solid; retention time ($t_R$)-7.0 min. [Whatman Partisil 5 ODS-3, 4.6×250 mm, 70:30:MeOH:0.05M Tris (pH 7.5), 1.5 mL/min.]; UV max (CH$_3$OH) 289 nm ($\epsilon$ 2 000), 283 (2 000), 203 (56 000), (0.1KOH) 300 (5 000), 295 (b 5 000), 255 (8 000), 215 (30 000); IR (CCl$_4$) 3536, 2951, 2926, 2878, 2855, 1743, 1270, 1239, cm$^{-1}$; $^1$H NMR (CDCl$_3$) δ 6.63 (s, 1), 6.49 (s, 1), 6.41 (s, 1), 5.94 (d, 1J-1 Hz), 5.87 (d, 1, J-1 Hz), 5.09 (d, 1, J-10.7), 4.83 (s, 1), 4.50 (m, 1). , 4.41 (s, 1), 4.19 (d, 1, J-4.7 Hz) 3.96 (dd, 1J-2, 11 Hz), 3.82 (s, 3), 3.65 (d, 1, J-4.3 Hz), 3.59 (s, 3), 3.23 (m, 1), 3.15 (m, 1), 2.87 (m, 2H), 2.77 (m, 1), 2.61 (m, 1), 2.49 (m, 1), 2.47 (d, 1, J-15 Hz), 2.35 (s, 3), 2.24. (d, 1, J-15 Hz), 2.18 (s, 3), 2.15 (s, 3); FABMS m/z (rel. intensity) 702 (8), 218 (4), 204 (8); B/E linked scan FABMS m/z 702→m/z (rel. intensity) 701 (100), 688 (4), 672 (6), 654 (24), 453 (44), 451 (28), 433 (48), 421 (20).

Anal. Calcd for C$_{37}$H$_{40}$N$_3$O$_9$S: 702.2485 (M+H−H$_2$O).

Part B. Treatment with Lithium Aluminum Hydride

Ecteinascidin 743 (1.0 mg, 1.3 μml), is dissolved in cold diethyl ether (0.5 mL, 0° C.). Lithium aluminum hydride (LAH) (ca. 0.5 mg, 13 μmol) is added, causing the immediate evolution of gas. The reaction mixture is stirred for 30 min., then warmed to 25° C. and stirred for 1 day. When HPLC analysis indicates no reaction after 1 day, another portion of LAH (ca. 0.5 mg) is added and gas is again produced. Addition of a third portion of LAH (ca. 0.5 mg), caused no further evolution of gas. HPLC analysis at this point is no longer practical due to excessive flocculent material in the reaction mixture. The mixture is stirred another 2 days, then quenched by slow addition of methanol (0.25 mL). Following removal of solvents under a stream of nitrogen, diethyl ether (10 mL) is added. The ethereal extract is filtered, washed with water (2×5 mL), and dried under a stream of nitrogen to give deacetylecteinascidin 743 (0.1 mg, 11%).

Deacetylecteinascidin 743 has the following physicochemical characteristics: pale yellow solid; $t_R$ 7.2 min. [Whatman Partisil 5 ODS-3, 4.6×250 mm, 70:30:MeOH:0.05M Tris (pH 7.5), 1.5 mL/min.]; IR (CCl$_4$) 3536, 2926, 2874, 2855, 1740, 1270 cm$^{-1}$; FABMS m/z (rel. intensity) 744 (6), 702 (18), 453 (20), 451 (16), 435 (10), 421 (16), 419 (18), 218 (20), 204 (80).

anal. Calcd for C$_{37}$H$_{40}$N$_3$O$_9$S: 702.2485 (M+H-H$_2$O). Found: 702.2438 (HRFABMS).

Part C. Treatment with Ozone

Ecteinascidin 743 (2.3 mg, 3.1 μmol) in methanol (10 mL) is cooled to −78°. Ozone (Welsbach model T-816 ozonator) is bubbled through the solution until it turns light blue (3 min). Dimethyl sulfide (20 μL, 250 μmol) is added and the solution is stirred, slowly warmed (1 hr.) to room temperature, and stirred for 1 hr. The product is dried under a stream of nitrogen, taken up in water (5 mL) and chloroform (5 mL), and the aqueous layer is extracted (3×5 mL), with chloroform to yield, after removal of solvent, an aqueous soluble portion (3.1 mg) and an organic-soluble portion (<0.5 mg). HPLC analysis of the aqueous-soluble portion revealed the presence of a complex mixture. Attempts to locate and purify the components of this mixture were unsuccessful.

EXAMPLE 8

Derivatives of Ecteinascidin 743

Part. A. Preparation of Mono- and Di-O-methylecteinascidins 743

A freshly prepared ethereal solution of diazomethane [from Diazald (Aldrich), 0.25 mL] is added to a solution of ecteinascidin 743 (1 mg, 1.3 μmol) in methanol (0.24 mL). The reaction is followed by HPLC [Whatman Partisil 5 ODS-3, 4.6×250 mm, 70:30: MeOH:0.05M Tris (pH 7.5), 1.5 mL/min.]. An initial product ($t_4$-11.2 min.) is observed immediately (3 min.). After 70 min. a second product ($t_R$-18.0 min.) is observed in a ca. 1:1 ratio with the initial product. The reaction is stopped after 130 min. by removing the solvents under a stream of nitrogen. Preparation HPLC [Whatman Partisil 10 ODS-3, 10×250 mm, 70:30: MeOH:0.05M Tris (pH 7.5), 2.8 mL/min.] of the reaction mixture afforded mono-O-methyl ecteinascidin 743 (0.3 mg, 29%) and di-O-methylecteinascidin 743 (0.5 mg, 48%).

Part B. Mono-O-methylecteinascidin 743

Mono-O-methylecteinascidin 743 has the following physicochemical characteristics: beige solid; $t_R$-11.2 min. [Whatman Partisil 5 ODS-3, 4.6×250 mm, 70:90:MeOH:0/05M Tris (pH 7.5), 1.5 mL/min.]; UV max (CH$_3$OH) 285 nm ($\epsilon$ 600), 201 (21 000), (0.1N KOH) 287 (600); IR (CCl$_4$) 2859, 2855, 2581, 1770, 1741, 1520, 1264, 1226, 1196, 1089, 1053 cm$^{-1}$; $^1$H NMR (CDCl$_3$) δ 6.62 (s, 1), 6.48 (s, 1), 6.41 (s,1), 6.03 (s, 1), 5.95 (s, 1), 5.72 (s, 1), 5.13 (d, 1, J-11.5 Hz), 4.81 (br s, 1), 4.50 (m, 2), 4.16 (d, 1, J-11.5 Hz), 4.05 (dd, 1, J-3, 12 Hz), 3.80 (s, 3), 3.76 (s, 3), 3.60 (s, 3), 3.58 (m, 1), 3.20 (m, 2), 2.88 (m, 2), 2.85 (m, 2), 2.63 (m, 1), 2.50 (m, 1), 2.37 (m, 1), 2.33 (s, 3), 2.27 (s, 3), 2.18 (s, 3), 2.03 (s, 3); FABMS m/z (rel. intensity) 758 (10), 477 (22), 470 (28), 218 (12), 204 (12); B/E linked scan FABMS m/z 758→m/z (rel. intensity) 757 (100), 744 (10), 730 (14), 724 (14), 712 (20), 495 (88), 477 (20), 475 (18), 465 (12), 463 (28).

Anal. Calcd for C$_{40}$H$_{44}$N$_3$O$_{10}$S:758.2747 (M+H-H$_2$O). Found: 758.2754 (HRFABMS).

Part C. Di-O-methylecteinascidin 743

Di-O-methylecteinascidin 743 has the following physicochemical characteristics: beige solid; $t_R$-18.0 min. [Whatman Partisil 5 ODS-3, 4.6×250 mm, 70:30:MeOH:0.05M Tris (pH 7.5), 1.5 mL/min.]; UV max (CH$_3$OH) 280 nm ($\epsilon$ 500), 205 (10 000), (0.1N KOH), 285 (700); IR (CCl$_4$) 2963, 2954, 2931, 2854, 1769, 1742, 1519, 1261, 1225, 1198, 1090, 1055, 1001, cm$^{-1}$; $^1$H NMR (300 MHz, CDCl$_3$) δ 6.78 (s, 1), 6.46 (s,1), 6.41 (s, 1), 6.03 (s, 1), 5.95 (s, 1), 5.14 (d, 1, J-10.1 Hz), 4.82 (br s, 1), 4.50 (m, 2), 4.12 (dd, 1, J-2, 5.5 Hz), 4.05 dd, 1, J-2, 11 Hz), 3.92 (s, 3), 3.83 (s, 3), 3.76 (s, 3), 3.66 (m, 1), 3.60 (s, 3), 3.23 (m, 2), 2.88 (m, 3), 2.65 (m, 1), 2.48 (m, 1), 2.35 (m, 1), 2.29 (s, 3), 2.24 (s, 3), 2.17 (s, 3), 2.03 (s, 3); FABMS m/z (rel. intensity) 772 (24), 509 (4), 491 (6), 477 (10), 218 (20), 204 (6); B/E linked scan FABMS m/z 772→m/z (rel. intensity) 771 (100), 758 (4), 742 (6), 726 (18),. 509 (100), 491 (30), 489 (30), 479 (20), 477 (40).

Anal. Calcd for $C_{41}H_{46}N_3O_{10}S$:772.2904 (M+H-$H_2O$). Found: 772.2891 (HRFABMS).

Part D. Preparation of Mono- and Dioxyecteinascidins 743

Aqueous hydrogen peroxide (30%, 0.5 μL) is added to a stirred methanolic solution (0.5 mL) of ecteinascidin 743 (1 mg, 1.4 μmol) cooled to 0° C. The reaction is followed by HPLC [Whatman Partisil 5 ODS-3, 4.6×250 mm, 70:30:MeOH:0.05M Tris (pH 7.5), 1.5 mL/min.]. The reaction mixture is stirred for 30 min., then warmed to 25° C. with stirring. After 1.5 hr., an additional aliquot of hydrogen peroxide (30%, 5 μL) is added after 27 hr. and the reaction mixture is stirred for another 2 days. HPLC analyses revealed a complex mixture (ca. 16 peaks). Preparative HPLC purification of this mixture affords monooxyecteinascidin 743 (0.2 mg, 20%) an dioxyecteinascidin 743 (0.4 mg, 38%).

Part E. Monooxyecteinascidin 743

Monooxyecteinascidin 743 has the following physicochemical characteristics; beige solid: $t_R$ 7.0 min. [Whatman Partisil 5 ODS3, 4.6×250 mm, 70:30:MeOH:0.05M Tris (pH 7.5), 1.5 mL/min.]; UV max ($CH_3OH$) 288 nm (ε 6 000), 281 (6 000), 235 (12 000), 201 (46 000), (0.1N KOH), 291 (8 000), 260 (10 000), 213 (58 000); IR ($CCl_4$) 2690, 2935, 1760, 1740, 1510, 1460, 1435, 1270, 1240, 1195, 1175, 1080 cm$^{-1}$; $^1$H NMR (300 MHz, $CDCl_3$) δ 6.69 (s, 1), 6.48 (s, 1), 6.47 (s, 1), 6.03 (s, 1), 5.95 (s, 1), 5.19 (s, 1), 5.10 (d, 1, J-11.3 Hz), 4.80 (s, 1), 4.73 (m, 1), 4.54 (br s, 2), 4.07 (d, 1, J-10 Hz), 3.85 (m, 1), 3.82 (s, 3), 3.63 (s, 3), 3.50 (m, 1), 3.23 (m, 1), 3.15 (m, 1), 3.03 (s, 3), 2.80 (m, 3), 2.62 (m, 1(, 2.49 (m, 1), 2.36 (s, 3), 2.26 (s, 3), 2.03 (s, 3); FABMS m/z (rel. intensity) 760 (16), 744 (10), 463 (6), 204 (22); B/E linked scan FABMS m/z 760→m/z (rel. intensity) 744 (100), 743 (100), 713 (76), 698 (30), 465 (34).

Anal. Calcd for $C_{39}H_{42}N_3O_{11}S$:760.2540 (M+H-$H_2O$). Found: 760.2563 (HRFABMS).

Part F. Dioxyecteinascidin 743

Dioxyecteinascidin 743 has the following physicochemical characteristics: beige solid; $t_R$ 4.2 min. [Whatman Partisil 5 ODS-3, 4.6×250 mm, 70:30:MeOH:0.05M Tris (pH 7.5), 1.5 mL/min.]; UV max ($CH_3OH$) 282 nm (ε 12 000), 235 (22 000), 201 (78 000), (0.1N KOH) 293 (14 000), 250 (20 000), 214 (63 000); IR ($CHCl_3$) 1770, 1740 cm$^{-1}$; $^1$H NMR (300 MHz, $CDCl_3$) methyl singlets; δ 3.89, 3.64, 2.33, 2.29, 2.10, 2.05; FABMS, m/z (rel. intensity) 776 (4), 760 (4), 463 (42); B/E linked scan FABMS m/z 776→m/z (rel. intensity) 759 (100), 713 (72), 463 (64), m/z 760→m/z (rel. intensity), 742 (100), 713 (34), 698 (28), 509 (36), 494 (45), 464 (30).

Anal. Calcd for $C_{39}H_{42}N_3O_{12}S$:776.2489 (M+H-$H_2O$). Found: 776.2523 (HRFABMS).

Part G. Preparation of Monoacetylecteinascidin 743

Ecteinascidin 743 (2 mg, 2.8 μmol) is dissolve din dry dichloromethane (0.5 mL). Acetic anhydride (10 μL, 28 μmol) and pyridine (20 μL, 56 μmol) are added and the reaction is stirred at 25° C. The reaction is followed by HPLC [Whatman Partisil 5 ODS-3, 4.5×250 mm, 70:30:MeOH:0.5M Tris (pH 7.5), 1.5 mL/min.]. After 1 day, stirring material is no longer detected. The solvents are removed under a stream of nitrogen and the product is purified by HPLC to yield acetylecteinascidin 743 (2.0 mg. 91%).

Acetylecteinascidin 743 has the following physicochemical characteristics: white solid; $t_R$11.5 min. [Whatman Partisil 5 ODS-3, 4.6×250 mm, 70:30:MeOH:0.5M Tris (pH 7.5), 1.5 mL/min.]; UV max ($CH_3OH$) 282 nm (ε 7 000), 201 (84 000), (0.1N KOH) 288 (11 000), 215 (62 000); IR ($CCl_4$) 3536, 2957 2932, 2857, 1771, 1743, 1507, 1457, 1430, 1368, 1320, 1270, 1196, 1168, 1110, 1089, 1054, 1032, 915 cm$^{-1}$; $^1$H NMR (300 MHz, $CDCl_3$) δ 6.61 (s, 1), 6.47 (s, 1), 6.45 (s, 1), 6.01 (s, 1), 5.95 (s, 1), 5.71 (s, 1), 5.12 (d, 1, J-11.5 Hz), 4.81 (s, 1), 4.49 (m, 2), 4.18 (d, 1, J-5 Hz), 4.04 (d, 1, J-11.5 Hz), 3.81 (s, 3), 3.61 (s, 3), 3.59 (d, 1, J-5 Hz), 3.21 (m, 1), 3.12 (m, 1), 2.88 (m, 2), 2.82 (m, 1), 2.61 (m, 1), 2.49 (m, 1), 2.37 (m, 1), 2.33 (c, 3), 2.28 (s, 3), 2.24 (s, 3) 2.18 (s, 3), 2.01 (s, 3); FABMS m/z (rel. intensity) 786 (64), 744 (14), 495 (6), 493 (6), 477 (6), 463 (12), 461 (4), 281 (28), 204 (40); EIMS (70 eV), m/z (rel. intensity) 768 (2), 458 (28), 443 (20), 430 (10), 416 (16), 403 (16), 385 (18), 375 (12), 360 (10), 274 (24), 259 (12), 245 (10), 231 (20), 217 (60), 203 (52), 189 (48), 174 (74), 160 (48), 146 (26), 133 (100), 115 (24); B/E linked scan FABMS m/z 786→m/z (rel. intensity) 771 (12), 755 (10), 743 (14), 739 (18), 728 (4), 697 (4), 495 (50), 493 (30), 477 (20), 475 (18), 463 (56), 461 (18).

Anal. Calcd for $C_{41}H_{44}N_3O_{11}S$:786.2697 (M+H-$H_2O$). Found: 786.2712 (HRFABMS).

Part H. Preparation of Di- and Tetraacetylecteinascidins 743

Ecteinascidin 743 (0.5 mg, 0.7 μmol) is stirred in a solution of pyridine-acetic anhydride (2:1, 2 mL) for 2 days. The solvents are removed under a stream of nitrogen and the residue is taken up in water (5 mL) and chloroform (5 mL). The organic layer is washed with water (3×5 mL) and dried ($MgSO_4$), and the solvent is removed to yield a mixture of di- and tetraacetyl derivatives (0.5 mg, 85%): pale yellow solid; FABMS m/z (rel. intensity) 912 (10), 844 (8), 828 (30), 537 (2), 535 (2), 519 (4), 505 (8), 463 (4), 218 (18), 205 (42), 204 (36).

Part I. Preparation of p-Bromobenzoylecteinascidin 743

Ecteinascidin 743 (2 mg, 2.8 μmol), p-bromobenzoyl chloride (3.2 mg, 14 μmol, Aldrich), pyridine (2 μL, 24 μmol), and methylene chloride (0.5 mL) are combined and stirred at room temperature for 39 h. The reaction is followed by HPLC [Whatman Partisil 5 ODS-3, 4.6×250 mm, 70:30:MeOH:0.05M Tris (pH 7.5), 1.5 mL/min.]. After 24 hr. additional amounts of p-bromobenzoyl chloride (ca. 3 mg) and pyridine 2 μL are added. The reaction is stopped after 39 hr. when there is no further change in the peak corresponding to the starting material. The product is purified by preparative HPLC [Whatman Partisil 10 ODS-3, 10×250 mm, 70:30–100:0 (step gradient) MeOH:0.05M Tris (pH 7.5), 2.8 mL/min.] to yield p-bromobenzoylecteinascidin 743 (2.4 mg, 96%).

p-Bromobenzoylecteinascidin 743 has the following physicochemical characteristics: white solid; UV max ($CH_3OH$) 280 nm (ε 8 000), 241 (31 000), 201 (90 000), 0.1N KOH) 290 (8 000), 238 (31 000), 215 (50 000); IR ($CCl_4$) 3533, 2954, 2929, 2873, 2854, 1770, 1745, 1592, 1509, 1485, 1463, 1450, 1431, 1400, 1369, 1321, 1264, 1197, 1173, 1152, 1136, 1119, 1089, 1072, 1053, 1032 cm$^{-1}$; $^1$H NMR (300 MHz, $CDCl_3$) δ 7.99 (d, 2, J-8.5 Hz), 7.61 (d, 2, J-8.5 Hz), 6.72 (s, 1), 6.62 (s, 1), 6.61 (s, 1), 6.00 (s, 1), 5.93 (s, 1), 5.71 (br, s, 1), 5.14 (d, 1, J-11.2 Hz), 4.82 (s, 1), 4.49 (br, s, 2), 4.17 (d, 1, J-4.7 Hz), 4.05 (dd, 1, J-11.2, 2.2 Hz), 3.80 (s, 3), 3.59 (d, 1, J-5.2 Hz), 3.53 (s, 3), 3.22 (m, 1), 3.15 (m, 1), 2.88 (m, 2), 2.82 (m, 1), 2.65 (m, 1), 2.52 (ddd, 1, J-16, 4, 4 Hz), 2.38 (br d, 1, J- 14 Hz), 2.33 (s, 3), 2.28 (s, 3), 2.19 (m, 1), 2.18 (s, 3), 2.02 (s, 3); FABMS m/z (rel. intensity) 928 (6), 926 (5), 880 (1), 848 (b 1), 744 (1), 509 (2), 495 (6), 493 (4), 477 (10), 463 (22), 218 (30), 204 (52).

Anal. Calcd for $C_{46}H_{45}BrN_3O_{11}S$:928.1938 (M+H-$H_2O$). Found: 928.1954 (HRFABMS).

EXAMPLE 9

Substructures of Ecteinascidin 743

From the spectral data on ecteinascidin 743, its derivatives and the analogous ecteinascidins, one can assign substructures of the molecule. Additionally, the NMR data and especially the $^1H$-$^{13}C$ heteronuclear correlation NMR data allow correlation of the six $CH_3$ groups and the three aromatic CH groups. HRFABMS studies show fragmentation of ecteinascidin 743 into 4 pieces;

$SCH_3$, $C_{11}H_8NO_3$, $C_{15}H_{17}NO_5$, and $C_{12}H_{14}NO_2$.

The molecular formulae of the three nitrogen-containing pieces, the very intense UV spectra, the aromatic $^{13}C$ NMR absorptions, and the aromatic $^1H$ NMR absorptions all suggest the presence of three trioxygenated tetrahydroisoquinoline units. The $C_{12}H_{14}NO_2$ fragment, the m/z 204 ion in the FAB mass spectrum, must contain the N-$CH_3$ that is absent in ecteinascidin 729, one aromatic hydroxyl, and the aromatic methyl (only two oxygens allowed in the formula).

EXAMPLE 10

Structures of the Ecteinascidins

Ecteinascidin (Et) 743 showed a "molecular" ion at 744.2648 by HRFABMS. In agreement with the "molecular"formula, $C_{39}H_{42}N_3O_{10}S$ (Δ 5.7 mmu)

the $^{13}C$ NMR spectrum contained 39 carbon signals and electron spectroscopy for chemical analysis (ESCA) indicated a single sulfur atom. Further careful analyses of these data have now resulted in elucidation of the structures of the ecteinascidins, particularly Et 743, as follows:

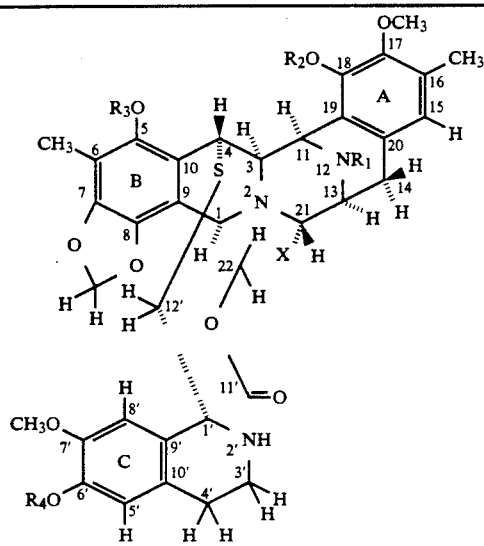

| Compound | X | $R_1$ | $R_2$ | $R_3$ | $R_4$ |
|---|---|---|---|---|---|
| Et 743 | OH | $CH_3$ | H | Ac | H |
| Et 743 (OMe) | $OCH_3$ | $CH_3$ | H | Ac | H |
| Et 729 | OH | H | H | Ac | H |
| Et 745 | H | $CH_3$ | H | Ac | H |
| Et 759A* | OH | $CH_3$ | H | Ac | H |
| Et 759B* | OH | $CH_3$ | H | Ac | H |
| Et 770 | CN | $CH_3$ | H | Ac | H |
| Et 756 | CN | H | H | Ac | H |
| deacetyl Et 743 | OH | $CH_3$ | H | H | H |
| mono-O-methyl Et 743 | OH | $CH_3$ | H | Ac | $CH_3$ |
| di-O-methyl Et 743 | OH | $CH_3$ | $CH_3$ | Ac | $CH_3$ |
| monooxy Et 743** | OH | $CH_3$ | H | Ac | H |
| dioxy Et 743*** | OH | $CH_3$ | H | Ac | H |
| monoacetyl Et 743 | OH | $CH_3$ | H | Ac | Ac |
| diacetyl Et 743 | OH | $CH_3$ | Ac | Ac | Ac |
| p-bromobenzoyl Et 743 | OH | $CH_3$ | H | Ac | p-$BrC_6H_4CO$ |

*N-oxide of Et 743.
**Oxidized at N-12.
***Oxidized at two positions.

Knowledge of this structure then permits assignment of the structures of the other ecteinascidins as shown above.

FABMS/MS (tandem mass spectrometry, employing a VG 70 SE 4F spectrometer) was critical in locating the three nitrogen atoms in three units of similar size and composition, differing mainly in the numbers of oxygens. The UV spectrum is unremarkable but agreed with that expected for a tris(multi-oxygenated benzene). A portion of the molecule (unit A) appeared to be identical to a unit in safracin B [J. Antibiot., (1983), 36, 1284–1289, and J. Antibiot., (1985), 38, 24–30] since the $^{13}C$ and $^1H$ chemical shifts were nearly the same, and the key FAB mass spectral peaks at m/z 204.1027 (Δ −0.2. mmu) and 218.1174 (Δ 0.7 mmu) were also prominent for safracin B. Heteronuclear multiple bond correlation (HMBC) spectroscopy confirmed unit A, as shown.

A second aromatic unit (unit B) was constructed from HMBC to overlap unit A. The latter observation had already been adumbrated by the FABMS/MS data, with the A and B units together with the m/z 495 ion.

The third aromatic unit (unit C) was also identified by HMBC, as shown. A proton can be attached to the pendant oxygen in unit C since mass spectral fragments associated with unit C shift by 14 mass units in di-O-methyl Et 743 and by 42 mass units in di-O-acetyl Et 743. By a similar argument, the acetyl group [$CH_3CO$—, δ ($^{13}C$) 20.4 and 168.3, δ ($^1H$) 2.28, HMBC, HETCOR] can be assigned to the pendant oxygen in unit B since fragments associated with it do not shift in either Et 743 derivative, whereas they are 42 mass units less in deacetyl Et 743. Unfortunately, the protons and carbons in unit C are not correlated by HMBC with those in units A or B or with the remaining units of the molecule, a methylene [—$CH_2$—, δ ($^{13}C$) 42.2, δ ($^1H$), 2.37 and 2.18, COSY, HETCOR] and a sulfide (—S—).

Chemical shift and lack-of-coupling arguments require the methylene carbon to be attached to the quaternary carbon of unit C as well as to the sulfide link; chemical shift arguments require the quaternary carbon in unit C (δ 64.7 ) to be attached to the nitrogen in that unit; the sulfide must by stability and chemical shift arguments be attached to the aryl methine (δ 42.2); and the carbonyl must by chemical shift arguments be attached to the quaternary carbon. The remaining bond should then join the nitrogen of unit C to the aminomethine carbon of unit B. However, the chemical shifts of the carbon ($\delta$ 82.0) and hydrogen ($\delta$ 4.50) are unexpectedly far downfield for a —CH(N<)$_2$ unit, but exactly that expected for a —CH(OH)—N< unit, as found in safracin B. Consequently, the structure of Et 743 is assigned as shown (X=OH, R$_1$=CH$_3$, R$_2$=H, R$_3$=Ac, R$_4$=H), the molecule undergoing dehydration during FABMS. The same phenomenon (dehydration, lack of FAB M+H) has been observed in FABMS on safracin B [*J. Antibiot.*, (1985), 38, 24–] and saframycin Mx1 [*Liebigs Ann. Chem.*, (1988), 475–481].

Confirmation of this carbinolamine hypothesis is provided by the negative ion HRFAB mass spectrum of 1 in a diethanolamine matrix, which gives M-H at 760.2514 (C$_{39}$H$_{42}$N$_3$O$_{11}$S, $\Delta$ 2.6 mmu). The hydroxyl is readily exchanged (cf. cyanide below). Treatment with a trace of methanol gives the next O-methyl analogue (X=OCH$_3$, R$_1$=CH$_3$, R$_2$=H, R$_3$=Ac, R$_4$=H; M-H 774.2679, C$_{40}$H$_{44}$N$_3$O$_{11}$S, $\Delta$ 1.8 mmu, by negative ion HRFABMS) for which the carbinolamine carbon, C-21, has shifted to $\delta$ 91.8 (CDCl$_3$).

The structure assigned is amply substantiated by mass spectrometric fragmentations. The relative stereochemistry assigned at C-1, C-3, C-11 and C-13 in Et 743 is derived from extensive NOE correlations, and is the same as in safracins and saframycins; that at C-21 is the same as in safracins and saframycins (where C-21 and H-21 appear with similar chemical shifts and coupling constant); that at C-4 is tentative, based on lack of observed coupling for H-3 and H-4; that at C-1 is arbitrary. The absolute stereochemistry shown is the same as in bromosafracin A, but is also arbitrary.

Assignment of the structure of Et 743 allows assignment of complete structures to the other ecteinascidins as well. Et 729 (X=OH, R$_1$=H, R$_2$=H, R$_3$=Ac, R$_4$=H), the most active antitumor agent, is the N-demethyl analogue (lacking $\delta$ 2.19); Et 745 (X=H, R$_1$=CH$_3$, R$_2$=H, R$_3$=Ac, R$_4$=H) arises from the reduction of the carbinolamine unit of Et 743 (replacement of OH by H); Et 770 (X=CN, R$_1$=CH$_3$, R$_2$=H, R$_3$=Ac, R$_4$=H) is the cyanoamine analogue (CN replacement of OH). Et 770 can be formed by treatment of Et 743 with KCN, and the corresponding new cyano compound (et 756, X=CN, R$_1$=H, R$_2$=H, R$_3$=Ac, R$_4$=H) is derived from Et 729 by like treatment. Et 759A and Et 759B (M-H$_2$O=C$_{39}$H$_{41}$N$_3$O$_{11}$S by HRFABMS) are believed to be N-oxides of ET 743.

The structures assigned herein to the ecteinascidins are related to those of the microbially derived safracins [see literature cited above] and saframycins [Arai, T. in "Natural Products Isolation, Separation Methods for Antimicrobials, Antivirals and Enzyme Inhibitors"; Wagman and Cooper Eds.; *J. Chromatogr. Lib.*, Vol. 43; Elsevier; Amsterdam, 1989; Chapter 5], as well a of the sponge-derived renieramycins [*J. Org. Chem.*, (1989), 54, 5822–5824 and *J. Am. Chem. Soc.*, (1982), 104, 265–269] and xestomycin [Gulavita, N. K.; Scheuer, P. J.; De Silva, E. D. Abstracts, Indo-United States Symp. on Bioactive Compounds from Marine Organisms, Goa, India, Feb. 23–27, 1989, p. 28], but show greater in vitro and in vivo antitumor activity than those reported for the saframycins or safracins. No antitumor activity has been reported for the renieramycins or xestomycin.

EXAMPLE 11

Bioactivities of the Ecteinascidins

The antimicrobial activities (vs. *M. luteus*) and the cytotoxic activities (vs. CV-1 cells) of the ecteinascidins and ecteinascidin 743 derivatives are shown in Table 1 and 2. Within experimental error (the dilutions are accurate to within a factor of 2 error), the activities of ecteinascidins 729 and 743 in this one assay are approximately equivalent and represent the most potent compounds in the series. Ecteinascidins 759A, 759B, and 770 are four to eight times less potent, and ecteinascidin 745 is some 32 times less potent than ecteinascidins 729 and 743. All of the derivatives of ecteinascidin 743 that were prepared have antimicrobial and cytotoxic activities. The monoacetyl derivative has enhanced activity over the original compound, whereas the other derivatives are two to eight times less active.

The ecteinascidins are not antiviral for Herpes simplex virus type I (HSV-1) or Vesicular stomatitis virus (VSV). Crude extracts have no antimicrobial activity against *Escherichia coli*, *Penicillium atrovenetum* and *Saccharomyces cerevisiae*. Ecteinascidin 743 is negative in the biomedical induction assay (BIA), an assay for DNA interaction.

The antimicrobial spectra of ecteinascidins 743 and 745 are shown in Table 3, and the antitumor activities of ecteinascidins 729, 743 and 745 are compared in Tables 4 and 5. The strong antitumor activity of the lower homologue, ecteinascidin 729, is especially noteworthy. This compound is clearly responsible for much of the antitumor activity of the crude extract. It is intriguing to find ecteinascidin 745 (deoxyecteinascidin 743) with greatly reduced activity (antimicrobial, cytotoxic, and antitumor).

TABLE 1

Anti-*M. luteus* Activities of the Ecteinascidins and Ecteinascidin 743 Derivatives (Zones of Inhibition in mm)

| Compound | mass (ng)/6.35-mm disk | | | | | |
|---|---|---|---|---|---|---|
| | 1600 | 800 | 400 | 200 | 100 | 50 |
| Ecteinascidin 729 | 18 | 16 | 15 | 11 | 8 | 7 |
| Ecteinascidin 743 | 23 | 20 | 14 | 13 | 12 | 9 |
| Ecteinascidin 745 | tr | — | — | — | — | — |
| Ecteinascidin 759A | 10 | 8 | tr | — | — | — |
| Ecteinascidin 759B | 15 | 13 | 10 | tr | — | — |
| Ecteinascidin 770 | 15 | 12 | 9 | tr | — | — |
| Ecteinascidin 743 Derivatives: | | | | | | |
| Deacetyl | 16 | 14 | 12 | 10 | 8 | tr |
| Mono-O-methyl | 14 | 14 | 11 | 8 | — | — |
| Di-O-methyl | 11 | 8 | — | — | — | — |
| Monoacetyl | 28 | 20 | 20 | 14 | 12 | 10 |
| p-Bromobenzoyl | 12 | 10 | 8 | — | — | — | tr = trace activity

TABLE 2

Anti-CV-1 Activities of the Ecteinascidins and Ecteinascidin 743 Derivatives (Zones of Inhibition in mm)

| Compound | mass (ng)/6.35-mm disk | | | | | |
|---|---|---|---|---|---|---|
| | 1600 | 800 | 400 | 200 | 100 | 50 |
| Ecteinascidin 729 | 18 | 16 | 13 | 10 | 10 | 9 |
| Ecteinascidin 743 | 28 | 23 | 23 | 20 | 16 | 14 |
| Ecteinascidin 745 | 14 | 9 | — | — | — | — |
| Ecteinascidin 759A | 16 | 16 | 10 | tr | — | — |
| Ecteinascidin 759B | 22 | 22 | 15 | 13 | 11 | tr |
| Ecteinascidin 770 | 25 | 24 | 20 | 16 | 14 | 10 |
| Ecteinascidin 743 Derivatives: | | | | | | |
| Deacetyl | 16 | 15 | 11 | — | — | — |
| Mono-O-methyl | 26 | 25 | 23 | 20 | 22 | 13 |
| Di-O-methyl | 18 | 16 | 13 | 17 | 15 | 13 |
| Monoacetyl | 30 | 28 | 25 | 22 | 22 | 18 |

TABLE 2-continued

Anti-CV-1 Activities of the Ecteinascidins
and Ecteinascidin 743 Derivatives
(Zones of Inhibition in mm)

| Compound | mass (ng)/6.35-mm disk | | | | | |
|---|---|---|---|---|---|---|
| | 1600 | 800 | 400 | 200 | 100 | 50 |
| p-Bromobenzoyl | 18 | 16 | 12 | 10 | — | — | tr = trace activity

TABLE 3

Antimicrobial Spectrum of Ecteinascidins 743 and 745
(Zones of Inhibition in mm around 6.35-mm disk)

| Microorganism | Ecteinascidin 743 (10 μg/disk) | Ecteinascidin 745 (5 μg/disk) |
|---|---|---|
| Bacillus subtilis | 25 | 0 |
| Bacillus subtilis syn | 26 | 0 |
| Klebsiella pneumoniae | 20 | 0 |
| Sarcina lutea | 27 | tr |
| Sarcina lutea sens. | 35 | 18 |
| Escherichia coli | 11 | 0 |
| Pseudomonas aeruginosa | 0 | 0 |
| Staphylococcus aureus | 19 | 0 |
| Mycobacterium avium | 17 | 0 |
| Streptococcus pyogenes | NT | tr |
| Saccharomyces cerevisiae | 0 | 0 |
| Penicillium oxalicum | 10 | 0 | tr = trace activity
NT = not tested

TABLE 4

Antitumor Activity of
Ecteinascidins 729, 743 and 745 vs. P388 Leukemia

| Compound | T/C (%) | Dose (mg/kg) |
|---|---|---|
| Ecteinascidin 729 | 214 | 0.0038 |
| Ecteinascidin 743 | 167 | 0.015 |
| Ecteinascidin 745 | 111 | 0.25 |

TABLE 5

Antitumor Activity of Ecteinascidin 729 vs. B16 Melanoma

| | T/C (%) | Dose (mg/kg) |
|---|---|---|
| Ecteinascidin 729 | 246 | 0.01 |

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. The substantially pure compound Ecteinascidin 729, free of cellular components of the marine tunicate Ecteinascidia turbinata, said compound having the following physicochemical characteristics: TLC (SiO$_2$) R$_4$-0.28 (3:1 ethyl acetate-methanol), 0.26 (9:1 chloroform-methanol); HPLC retention time, 15.7 min. [Whatman Partisil 10 ODS-3, 10×250 mm, 70:30 methanol-aqueous Tris (0.05M, pH 7.5), 2.8 mL/min.]; UV max (CH$_3$OH), 202 nm (ε 61 000), 244 (sh) (11 000), 283 (5 000), 289 (4 700), (0.1N HCl) 204 (61 000), 244 (sh) (9 600), 283 (4 800), 289 (4 500), (0.1N KOH) 215 (33 800), 258 (8 200), 290 (6 400); IR (CCl$_4$), 3555, 3535, 2953, 2927, 2855, 1770, 1742, 1504, 1466, 1462, 1454, 1432, 1369, 1239, 1196, 1168, 1122, 1100, 1086, 1054, 1032, 997, 960 cm$^{-1}$; $^1$H NMR (360 MHz, CDCl$_3$) ε 6.63 (s, 1H), 6.48 (s, 1H), 6.44 (s, 1H), 6.04 (d, J-0.7 Hz, 1H), 5.95 (d, J-0.9 Hz, 1H), 5.15 (d, J-10.7 Hz, 1H), 4.84 (bs, 1H), 4.52 (d, J-3.5 Hz, 1H), 4.48 (bs, 1H), 4.38 (d, J-4.9 Hz, 1H), 4.04 (d, J-11 Hz, 1H), 3.78 (s, 3H), 3.62 (s, 3H), 3.61 (m, 2H), 3.10 (m, 1H), 3.02 (d, J-18 Hz, 1H), 2.90 (dd, J-9, 18 Hz, 1H), 2.80 (m, 1H), 2.60 (m, 1H), 2.50 (m, 1H), 2.35 (m, 1H), 2.31 (s, 3H), 2.27 (s, 3H), 2.20 (m, 1H), 2.03 (s, 3H); FABMS m/z (rel. intensity) 730.2493 (30), 495 (2), 493 (2), 481 (2), 479 (2), 463 (4), 461 (2), 449 (4), 205 (8), 204 (8), 190 (8); B/E linked scan on m/z 729, m/z 711, 696, 683, 509, 495, 481, 479, 461, 449; optical rotation [α]$_D^{25}$+112° (c 0.01, CH$_3$OH).

2. The substantially pure compound Ecteinascidin 743, free of cellular components of the marine tunicate Ecteinascidia turbinata, said compound having the following physicochemical characteristics: TLC (SiO$_2$) R$_f$-0.58 (3:1 ethyl acetate-methanol), 0.44 (9:1 chloroform-methanol); HPLC retention time, 18.8 min. [Whatman Partisil 10 ODS-3, 10×250 mm, 70:30 methanol-aqueous Tris (0.05M, pH 7.5), 2.8 mL/min.]; UV max (CH$_3$OH) 202 nm (ε 81 000), 240 (sh) (15 000), 284 (6 600), 289 (6 400), (0.1N HCl) 205 (76 000), 240 (sh), (12 000), 285 (7 500), 289 (7 200), (0.1N KOH) 216 (50 000), 256 (12 700) 290 (9 000); IR (CCl$_4$) 3549, 3530, 2992 (weak), 2929, 2848, 2803 (weak), 1764, 1739, 1597 (weak), 1511, 1501, 1460, 1445, 1425, 1365, 1350, 1195, 1160, 1115, 1102, 1098, 1082, 1058, 1048, 1024, 990, 950, 915, 907, cm$^{-1}$; $^1$H NMR (500 MHz, CDCl$_3$) δ 6.62 (s, 1H), 6.48 (s, 1H), 6.46 (s, 1H), 6.03 (d, J-1.2 Hz, 1H), 5.95 (d, J-1.3 Hz, 1H), 5.7 (bs, exchanges, 1H), 5.14 (dd, J-0.9, 11.3 Hz, 1H), 4.83 (bs, 1H), 4.50 (d, J-3.3 Hz, 1H), 4.50 (bs, 1H), 4.18 (d, J-4.2 Hz, 1H), 4.06 (dd, J-b 2.5, 11.3 Hz, 1H), 3.81 (s, 3H), 3.63 (s, 3H), 3.59 (bd, J-4.4 Hz, 1H), 3.23 (m, 1H), 3.14 (ddd, J-11, 10, 4 Hz, 1H), 2.91 (bd, J-18 Hz, 1H), 2.88 (dd, J-9, 18 Hz, 1H), 2.82 (m, 1H), 2.62 (ddd, J-16, 10, 4 Hz, 1H), 2.49 (ddd, J-16, 4, 4 Hz, 1H), 2.37 (bd, J-13.9 Hz, 1), 2.33 (s, 3H), 2.28 (s, 3H), 2.19 (s, 3H), 2.18 (d, J-13. 9 Hz, 1H), 2.04 (s, 3H); $^{13}$C NMR (75.4 MHz and 125.7 MHz, CDCl$_3$) δ 9.6 (q), 15.7 (1),20.4 (q), 24.1 (t), 28.7 (t), 39.6 (t), 41.3 (q), 42.1 (t), 42.1 (d), 54.8 (d), 55.0 (q), 55. 9 (d), 57.7 (d), 57.8 (d), 60.2 (q), 61.3 (t), 64.6 (s), 82.0 (d), 101.6 (t), 109.8 (d), 112.5 (s), 114.1 (d), 115.9 (s), 118.1 (s), 120.9 (d), 121.9 (s), 126.0 (s), 129.2 (s), 129.2 s), 131.5 (s), 140.5 (s), 141.3 (s), 143.0 (s), 144.3 (s), 144.5 (s), 145.1 (s), 147.5 (s), 168.3 (s), 172.5 (s); FABMS m/z (rel. intensity) 744.2648 (100), 699.2766 (4), 495.2064 (15), 477.1979 (15), 475 (9), 463.1837 (25), 281 (39), 204.1027 (71); LC/FABMS m/z (rel. intensity) 744 (34), 495 (12), 493 (16), 477 (14), 475 (10), 463 (14), 234 (42), 218 (64), 204 (100), 189 (62), 174 (28), 160 (22); EIMS m/z 217.0737305, 191.0941620, 176.0696716; ESCA (mole percent) C (73.1), O (20.4), N (5.2), S (1.3); optical rotation [α]$_D^{25}$+114° (c 0.1, CH$_3$OH); or a derivative thereof selected from the group consisting of:

deacetyl-, dioxy-, diacetyl-, monoacetyl-, mono-O-methyl-, di-O-methyl-, monooxy-, tetracetyl-, or p-bromobenzoyl.

3. The substantially pure compound Ecteinascidin 745, free of cellular components of the marine tunicate Ecteinascidia turbinata, said compound having the following physicochemical characteristics: TLC (SiO$_2$) R$_4$-0.42 (3:1 ethyl acetate-methanol), 0.38 (9:1 chloroform-methanol); HPLC retention time, 29.8 min. [Whatman Partisil 10 ODS-3, 10×250 mm, 70:30 methanol-aqueous Tris (0.05M, pH 7.5), 2.8 mL/min.]; UV max (CH$_3$OH) 202 (ε 52 000), 240 (sh) (11 000), 281 (5 600), 287 (5 400), (0.1N HCL), 204 (51 000), 240 (sh) (9 500), 281 (5 200), 287 (5 200), (0.1N KOH), 215 (36 000), 254 (8 500), 290 (5 900), 298 (5 800); IR (CCl$_4$) 3554, 3535, 2955, 2927, 2871, 2855, 1770, 1744, 1518, 1507, 1270, 1238, 1195, 1163, 1088, 1056 cm$^{-1}$; $^1$H NMR (360 MHz, CDCl$_3$), δ 6.62 (s, 1H), 6.52 (s, 1H), 6.47 (s, 1H), 6.02 (d, J-1.2 Hz, 1H), 5.97 (d, J-1.2 Hz, 1H), 5.74 (bs, exchanges, 1H), 5.14 (d, J-11.2 Hz, 1H), 4.5 (bs, 1H), 4.22 (bs, 1H), 4.11 (dd, J-2, 11 Hz, 1H), 3.79 (s, 3H), 3.68 (s, 1H), 3.63 (s, 3H), 3.31 (m, 1H), 3.23 (bs, 1H), 3.11 (m, 2H), 2.93 (m, 2H), 2.69 (m, 2H), 2.54 (m, 2H), 2.44 (d, J-14 Hz, 1H), 2.33 (s, 3H), 2.28 (s, 3H), 2.18 (s, 3H), 2.13 (m, 1H), 2.04 (s, 3H), ; FABMS m/z (rel. intensity) 746.2775 (100), 699 (8), 631 (8), 629 (8), 495 (19), 479 (42), 477 (52), 463 (36), 205 (64), 204 (64); LC/FABMS m/z (rel. intensity) 746 (44), 495 (18), 477 (20), 463 (32), 218 (42), 204 (100), 189 (62), 176 (32), 160 (20); optical rotation $[\alpha]_D^{25}$+50° (c 0.1, CH$_3$OH).

4. The substantially pure compound Ecteinascidin 759A, free of cellular components of the marine tunicate *Ecteinascidia turbinata*, said compound having the following physicochemical characteristics: TLC (SiO$_2$) R$_f$ 0.6 (3:1 ethyl acetate-methanol), 0.3 (9:1 chloroform-methanol); HPLC retention time, 11.0 min. [Whatman Partisil 10 ODS-3, 10×250 mm, 70:30 methanol-aqueous Tris (0.05M, pH 7.5), 2.8 mL/min.]; UV max (CH$_3$OH) 203 nm (ε 43 000), 250 (sh) (6 500), 281 (3 000), 288 (2 600), (0.1N HCl) 205 (44 000), 250 (sh) (7 600), 281 (4 500), 288 (4 400), (0.1N KOH) 216 (39 000), 249 (3 900), 294 (4 600); IR (CCl$_4$) 3696, 3555, 3532, 2926, 2854, 1770, 1744, 1670, 1466, 1252, 1240, 1194, 1091 cm$^{-1}$; FABMS m/z (rel. intensity) 760.2563 (58), 581 (24), 493 (16), 463 (80), 461 (100); LC/FABMS m/z (rel. intensity) 760 (26), 509 (12), 493 (12), 463 (24), 449 (16), 246 (26), 232 (32), 224 (62), 218 (5), 204 (100), 189 (56), 174 (18), 160 (16); optical retention $[\alpha]_D^{25}$+130° (c 0.05, CH$_3$OH).

5. The substantially pure compound Ecteinascidin 759B, free of cellular components of the marine tunicate *Ecteinascidia turbinata*, said compound having the following physicochemical characteristics: TLC (SiO$_2$) R$_f$ 0.6 (3:1 ethyl acetate-methanol), 0.3 (9:1 chloroform-methanol); HPLC retention time, 13.9 min. [Whatman Partisil 10 ODS-3, 10×250 mm, 70:30 methanol-aqueous Tris (0.05M, pH 7.5), 2.8 mL/min.]; UV max (CH$_3$OH) 208 nm (ε 60 000), 288 (4 800), 293 (4 500), (0.1N HCl) 209 (64 000), 288 (7 100), 293 (7 100), (0.1N KOH) 220 (45 000), 260 (10 000), 298 (7 600); IR (CCl$_4$), 3555, 2933, 1770, 1743, 1590, 1514, 1465, 1453, 1446, 1431, 1368, 1356, 1330, 1288, 1264, 1240, 1193, 1163, 1124, 1110, 1089, 1032, 1006, 821 cm$^{-1}$; FABMS m/z (rel. intensity) 760.2519 (100), 744 (71), 730 (19), 493 (29), 477 (43), 463 (76); LC/FABMS m/z (rel. intensity) 760 (38), 508 (8), 493 (18), 463 (26), 475 (14), 248 (30), 234 (48), 218 (86), 204 (100), 189 (56), 176 (26), 160 (32); optical rotation $[\alpha]_D^{25}$+167° (c 0.1, CH$_3$OH).

6. The substantially pure compound Ecteinascidin 770, free of cellular components of the marine tunicate *Ecteinascidia turbinata*, said compound having the following physicochemical characteristics: TLC (SiO$_2$) R$_f$ 0.6 (3:1 ethyl acetate-methanol), 0.3 (9:1 chloroform-methanol); HPLC retention time, 12.0 min. [Whatman Partisil 10 ODS-3, 10×250 mm, 70:30 methanol-aqueous Tris (0.05M, pH 7.5), 2.8 mL/min.]; UV max (CH$_3$OH) 342 nm (ε 3 200), 329 (3 900), 299 (22 000), 263 (25 000), 240 (58 000), 234 (55 000), 216 (66 000), (0.1N HCl) 342 (4 900), 329 (5 700), 299 (24 000), 263 (29 000), 240 (58 000), 234 (57 000), 216 (71 000), (0.1N KOH) 342 (3 700), 329 (4 900), 299 (22 000), 263 (28 000), 240 (58 000), 234 (57 000), 227 (57 000); IR (CCl$_4$) 3555, 3535, 3484, 2929, 2910, 1770, 1742, 1607, 1516, 1509, 1504, 1494, 1462, 1450, 1433, 1325, 1237, 1193 cm$^{-1}$; $^1$H NMR (300 MHz, CDCl$_3$), ε 6.60 (s, 1H), 6.47 (s, 1H), 6.45 (s, 1H), 6.05 (s, 1H), 5.98 (s, 1H), 5.02 (d, J-11.4 Hz, 1H), 4.57 (bs, 1H), 4.32 (bs, 1H), 4.28 (d, J-5.3 Hz, 1H), 4.18 (d, J-2.5 Hz, 1H), 4.12 (dd, J-2.1, 11.5 Hz, 1H), 3.78 (s, 3H), 3.62 (s, 3H), 3.50 (d, J-5 Hz, 1H), 3.42 (m, 1H), 3.10 (ddd, J-4, 10, 11 Hz, 1H), 2.94 (m, 2H), 2.79 (m, 1H), 2.61 (m, 1H), 2.47 (m, 1H), 2.34 (m, 1H), 2.32 (s, 3H), 2.27 (s, 3H), 2.20 (s, 3H), 2.09 (m, 1H), 2.04 (s, 3H); FABMS m/z (rel. intensity) 771.2700 (48), 760 (8), 744 (20), 723 (12), 488 (12), 463 (14), 461 (20), 205 (50), 204 (80); optical rotation $[\alpha]_D^{25}$+52° (c 0.1, CH$_3$OH).

* * * * *

UNITED STATES PATENT AND TRADEMARK OFFICE
CERTIFICATE OF CORRECTION

PATENT NO. : 5,089,273
DATED : February 18, 1992
INVENTOR(S) : Rinehart et al.

It is certified that error appears in the above-identified patent and that said Letters Patent is hereby corrected as shown below:

Column 1, line 4, insert the following:

--STATEMENT OF GOVERNMENT SUPPORT

Support for this invention was received from the National Institute of Allergy and Infectious Diseases under Grant No. AI 04769 and the National Institute of General Medical Sciences under Grant No. GM 27069. Thus the government of the United States of America has certain rights in this invention.--

Signed and Sealed this

Fifth Day of July, 1994

*Attest:*

BRUCE LEHMAN

*Attesting Officer*     Commissioner of Patents and Trademarks